(12) United States Patent
Jedrzejewski et al.

(10) Patent No.: US 11,422,989 B2
(45) Date of Patent: Aug. 23, 2022

(54) SCORING SYSTEM FOR DIGITAL ASSESSMENT QUALITY

(71) Applicant: Pearson Education, Inc., Bloomington, MN (US)

(72) Inventors: Krzysztof Jedrzejewski, Poznań (PL); Quinn Lathrop, Denver, CO (US); Kacper Lodzikowski, Poznań (PL); Mikolaj Olszewski, Bydgoszcz (PL); Mateusz Otmianowski, Poznań (PL); Malgorzata Schmidt, Poznań (PL)

(73) Assignee: PEARSON EDUCATION, INC., Bloomington, MN (US)

( * ) Notice: Subject to any disclaimer, the term of this patent is extended or adjusted under 35 U.S.C. 154(b) by 367 days.

(21) Appl. No.: 16/383,440

(22) Filed: Apr. 12, 2019

(65) Prior Publication Data

US 2020/0250160 A1    Aug. 6, 2020

Related U.S. Application Data

(63) Continuation-in-part of application No. 16/267,281, filed on Feb. 4, 2019.

(51) Int. Cl.
*G06F 16/215* (2019.01)
*G06F 16/25* (2019.01)
*G06F 17/18* (2006.01)

(52) U.S. Cl.
CPC .......... *G06F 16/215* (2019.01); *G06F 16/252* (2019.01); *G06F 17/18* (2013.01)

(58) Field of Classification Search
CPC ... G06F 16/215; G06F 16/2465; G06F 16/252
USPC .......................................... 707/603, 758, 776
See application file for complete search history.

(56) References Cited

U.S. PATENT DOCUMENTS

| | | | |
|---|---|---|---|
| 7,930,262 B2 * | 4/2011 | Friedlander | G06N 5/04 706/62 |
| 9,646,250 B1 | 5/2017 | Indurthi et al. | |
| 2008/0228747 A1 * | 9/2008 | Thrall | G06Q 50/20 |
| 2009/0162827 A1 | 6/2009 | Benson et al. | |
| 2010/0159432 A1 * | 6/2010 | German | G06Q 10/10 434/350 |
| 2013/0226674 A1 * | 8/2013 | Field | G06Q 50/20 705/7.38 |
| 2013/0246339 A1 * | 9/2013 | Kendrena | G06F 16/285 707/602 |
| 2014/0195466 A1 | 7/2014 | Phillipps et al. | |

(Continued)

*Primary Examiner* — Dangelino N Gortayo
(74) *Attorney, Agent, or Firm* — Quarles & Brady LLP

(57) ABSTRACT

Systems and methods of the present invention may be used to determine metrics and health scores for content that may correspond to an educational course or textbook, which may be in a digital format. The metrics and health scores may be determined at the assessment-item-part-level, assessment-item-level, section-level, chapter-level, and title-level, and may be used to quantitatively assess how well the corresponding content is performing based on responses submitted to assessment item parts of the content by one or more responders. The assessment-item-part-level metrics may include difficulty and discrimination values, scores, weights, and reliability values, which may be determined in whole or in part using maximum likelihood estimation methods based on a modified two parameter item response model.

17 Claims, 42 Drawing Sheets

(56) References Cited

U.S. PATENT DOCUMENTS

| | | | |
|---|---|---|---|
| 2015/0079576 A1* | 3/2015 | Obae | G06Q 50/20 |
| | | | 434/350 |
| 2015/0348433 A1* | 12/2015 | Gatterbauer | G06Q 10/101 |
| | | | 434/353 |
| 2017/0261949 A1 | 9/2017 | Hoffmann et al. | |
| 2018/0176312 A1 | 6/2018 | Smietana et al. | |
| 2018/0308473 A1 | 10/2018 | Scholar | |
| 2018/0366019 A1* | 12/2018 | Zertuche | G06Q 50/20 |
| 2019/0139428 A1* | 5/2019 | Hatton | G09B 19/00 |
| 2019/0189022 A1* | 6/2019 | Kokku | G09B 5/065 |
| 2019/0378429 A1 | 12/2019 | Panuganty et al. | |

\* cited by examiner

| Difficulty value (formative) | Chance of correct response | Band description | Difficulty score |
|---|---|---|---|
| -10.0 – -2.5 | 100% – 95% | very easy | 0% |
| -2.5 – -2.1 | 95% – 91% | very easy | 0% – 50% |
| -2.1 – 1.7 | 91% – 85% | easy | 50% – 100% |
| 1.7 – 2.1 | 85% – 15% | of medium difficulty | 100% |
| 2.1 – 2.5 | 15% – 9% | hard | 100% – 50% |
| 2.5 – 2.9 | 9% – 5% | very hard | 50% – 0% |
| 2.9 – 10.0 | 5% – 0% | very hard | 0% |

| Difficulty value (summative) | Chance of correct response | Band description | Difficulty score |
|---|---|---|---|
| -100 – -32 | 100% — 98% | very easy | 0% |
| -30 – -24 | 98% — 97% | very easy | 0% — 50% |
| | 98% — 95% | easy | 50% — 100% |
| | 95% — 25% | of medium difficulty | 100% |
| | 25% — 20% | hard | 100% — 50% |
| 14 – 40 | 20% — 15% | very hard | 50% — 0% |
| 42 – 100 | 15% — 0% | very hard | 0% |

| Assessment item usage value | Band description | Assessment item usage score |
|---|---|---|
| 66%—100% | Very high | 100% |
| 33%—66% | High | 100% |
| | Medium | 33%—100% |
| 0%—33% | Low | 0%—33% |
| 0%—0.5% | Very low | 0% |

| Assessment item part health score difference band and description | Assessment item part health score difference score |
|---|---|
| Similar | 100% |
| Similar | 85% — 100% |
| Different | 50% — 85% |
| Different | 20% — 50% |
| Very different | 0% — 20% |

FIG. 11F

SCORING SYSTEM FOR DIGITAL ASSESSMENT QUALITY

FIELD OF THE INVENTION

This disclosure relates to the field of systems and methods for evaluating the latent abilities of responders to assessment item parts of a group of assessment items and evaluating the quality of the assessment item parts, assessment items, sections, chapters, and titles using virtual computing environments.

CROSS REFERENCE TO RELATED APPLICATIONS

This application claims priority to U.S. Non-Provisional patent application Ser. No. 16/267,281, filed Feb. 4, 2019, which is incorporated by reference in its entirety for all purposes.

SUMMARY OF THE INVENTION

In an example embodiment, a system may include a computer processor, an electronic communication network, the computer processor being in electronic communication with a client computer device via the electronic communication network, a source database in electronic communication with the computer processor that stores assessment data corresponding to a plurality of assessment items, and a computer memory in electronic communication with the computer processor and configured to store computer-readable instructions When executed, the instructions may cause the computer processor to retrieve the assessment data from a source database, determine first assessment item part health scores for each of a plurality of assessment item parts of an assessment item of the plurality of assessment items, generate a first user interface, and cause the first user interface to be displayed at a screen of the client computer device.

Determining an assessment item part health score for an assessment item part of the plurality of assessment item parts may include determining assessment-item-part-level metric values for a plurality of assessment-item-part-level metrics for the assessment item part based on responses submitted to the plurality of assessment item parts by a sample population of responders, determining assessment-item-part-level metric scores for each of the plurality of assessment-item-part-level metrics based on the assessment-item-part-level metric values, assigning assessment-item-part-level weight values to each of the plurality of assessment-item-part-level metrics, determining assessment-item-part-level reliability values for each of the plurality of assessment-item-part-level metrics based on at least a size of the sample population of responders, and determining the assessment item part health score for the assessment item part based on the assessment-item-part-level metric scores, the assessment-item-part-level weight values, and the assessment-item-part-level reliability values. The first user interface may include the assessment-item-part-level metric scores.

In some embodiments, the instructions, when executed, may cause the computer processor to determine an assessment item health score for the assessment item by determining assessment-item-level metric values for a plurality of assessment-item-level metrics for the assessment item based at least on the first assessment item part health scores, determining assessment-item-level metric scores for each of the plurality of assessment-item-level metrics based on the assessment-item-level metric values, assigning assessment-item-level weight values to each of the plurality of assessment-item-level metrics, determining assessment-item-level reliability values for each of the plurality of assessment-item-level metrics, and determining the assessment item health score for the digital assessment item based on the assessment-item-level metric scores, the assessment-item-level weight values, and the assessment-item-level reliability values. The instructions, when executed, may further cause the computer processor to generate a second user interface that includes the assessment item health score and the assessment-item-level metric scores and cause the second user interface to be displayed at the client computer device.

In some embodiments, the plurality of assessment-item-part-level metrics may include at least a difficulty metric, a discrimination metric, and a hint change metric. The difficulty metric may correspond to an estimate of assessment item part difficulty. The discrimination metric may correspond to an estimate of an ability of a given assessment item part to discriminate between responders having different ability levels. The hint change metric may correspond to an estimate of how assessment item part difficulty is affected by hint usage.

In some embodiments, determining the assessment-item-part-level metric values for the plurality of assessment-item-part-level metrics for the assessment item part based on responses submitted to the plurality of assessment item parts by the sample population of responders may include determining a difficulty metric value, a discrimination metric value, and a hint change metric value for the assessment item part based on the assessment data and a modified two-parameter item response theory model.

In some embodiments, determining the difficulty metric value, the discrimination metric value, and the hint change metric value for the assessment item part may include iteratively applying a gradient descent optimization algorithm and a loss function to at least a portion of the assessment data according to the modified two-parameter item response theory model to determine the difficulty metric value, the discrimination metric value, and the hint change metric value.

In some embodiments, the loss function may include a sum of a cross entropy component, an ability mean component, and an ability standard deviation component.

In some embodiments, the assessment-item-level metrics may include one or more of an assessment item usage metric corresponding to a percentage of responders that used the assessment item to all responders that used assessment items in a section, the section comprising the assessment item, an assessment item completion metric corresponding to a percentage of responders that completed the assessment item to all responders that used the assessment item, a difference in assessment item part usage metric corresponding to a difference between a first number of responders that submitted at least one response to a most often used assessment item part of the assessment item and a second number of responders that submitted at least one response to a least often used assessment item part of the assessment item, an unused assessment item part metric corresponding to a percentage of unused assessment item parts of the assessment item, an assessment item part health score difference metric corresponding to an average difference between each of a plurality of assessment item part health scores corresponding to the assessment item, the plurality of assessment item part health scores including the first assessment item part health scores, an assessment item alignment metric corresponding to an estimate of how completing a formative assessment item of the assessment items affects responder performance on a corresponding summative assessment item of the assessment items, and an assessment item part health score average metric corresponding to an average of the plurality of assessment item part health scores.

In some embodiments, at least a portion of the assessment-item-part-level metric values may be calculated by first and second general purpose graphics processing unit instances operating in parallel.

In an example embodiment, a system may include a computer processor, a source database in electronic communication with the computer processor that stores assessment data corresponding to a plurality of assessment items, and a computer memory in electronic communication with the computer processor and configured to store computer-readable instructions.

When executed the instructions may cause the computer processor to retrieve the assessment data from the source database, determine a content health score for content of a hierarchical content level, generate a user interface that includes the content health score, and cause the user interface to be displayed at a screen of a client computer device in electronic communication with the computer processor. Determining the content health score may include determining metric values for a plurality of metrics for the content based on responses submitted to one or more of the plurality of digital assessment items by a sample population of responders, the plurality of metrics corresponding to the hierarchical content level of the content, determining metric scores for the plurality of metrics based on the metric values, assigning respective weight values to each of the plurality of metrics for the content, determining respective reliability values for each of the plurality of metrics, and determining the content health score for the content based on the metric scores, the weight values, and the reliability values. The user interface may further include the metric scores.

In some embodiments, determining respective reliability values for each of the plurality of metrics may include determining respective reliability values for each of the plurality of metrics for the content based on at least a size of the sample population of responders.

In some embodiments, determining the content health score for the content based on the metric scores, the weight values, and the reliability values may include calculating a first term, calculating a second term, and dividing the first term by the second term. The first term may be calculated by calculating a first plurality of products, where each of the first plurality of products corresponds to a respective metric of the plurality of metrics for the content, where the first plurality of products includes a first product of a metric score of the metric scores, a weight value of the weight values, and a reliability value of the reliability values. The second term may be calculated by calculating a second plurality of products, where each of the second plurality of products corresponds to a respective metric of the plurality of metrics for the content, and where the second plurality of products comprises a second product of the weight value and the reliability value.

The above features and advantages of the present invention will be better understood from the following detailed description taken in conjunction with the accompanying drawings.

BRIEF DESCRIPTION OF THE DRAWINGS

FIGS. 10B-10J illustrate tables depicting relationships between assessment-item-part-level metric values and assessment-item-part-level metric scores that may be used in determining assessment item part health scores, in accordance with an embodiment.

FIGS. 11B-11H illustrate tables depicting relationships between assessment-item-level metric values and assessment-item-level metric scores that may be used in determining assessment item health scores, in accordance with an embodiment.

DETAILED DESCRIPTION

Figure 1:
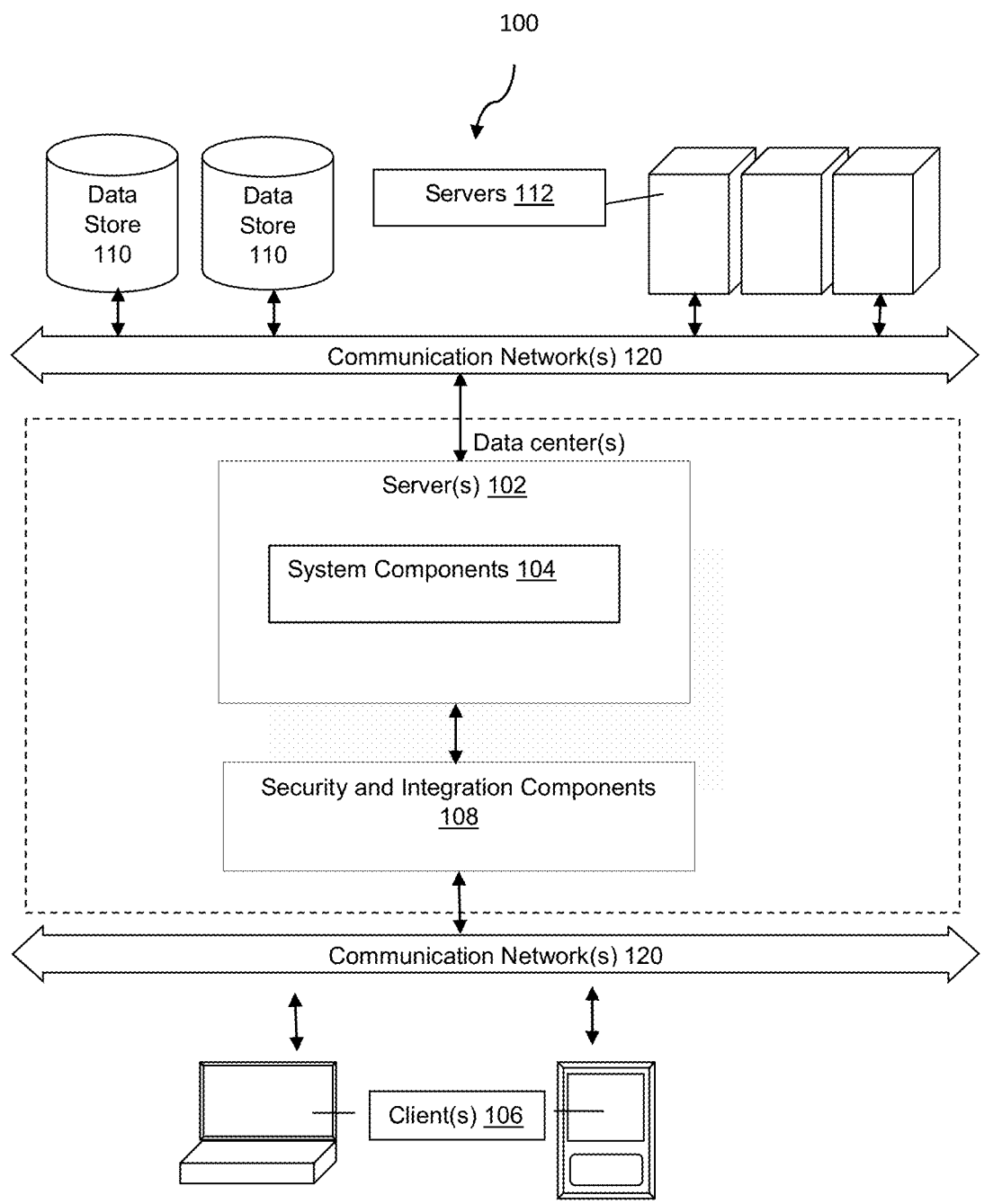
FIG. 1 illustrates a system level block diagram showing one or more data stores, data centers, servers, and clients of a distributed computing environment, in accordance with an embodiment.

The present inventions will now be discussed in detail with regard to the attached drawing figures that were briefly described above. In the following description, numerous specific details are set forth illustrating the Applicant's best mode for practicing the invention and enabling one of ordinary skill in the art to make and use the invention. It will be obvious, however, to one skilled in the art that the present invention may be practiced without many of these specific details. In other instances, well-known machines, structures, and method steps have not been described in particular detail in order to avoid unnecessarily obscuring the present invention. Unless otherwise indicated, like parts and method steps are referred to with like reference numerals.

FIG. 1 illustrates a non-limiting example of a distributed computing environment 100, which includes one or more computer server computing devices 102, one or more client computing devices 106, and other components that may implement certain embodiments and features described herein. Other devices, such as specialized sensor devices, etc., may interact with client 106 and/or server 102. The server 102, client 106, or any other devices may be configured to implement a client-server model or any other distributed computing architecture.

Server 102, client 106, and any other disclosed devices may be communicatively coupled via one or more communication networks 120. Communication network 120 may be any type of network known in the art supporting data communications. As non-limiting examples, network 120 may be a local area network (LAN; e.g., Ethernet, Token-Ring, etc.), a wide-area network (e.g., the Internet), an infrared or wireless network, a public switched telephone networks (PSTNs), a virtual network, etc. Network 120 may use any available protocols, such as (e.g., transmission control protocol/Internet protocol (TCP/IP), systems network architecture (SNA), Internet packet exchange (IPX), Secure Sockets Layer (SSL), Transport Layer Security (TLS), Hypertext Transfer Protocol (HTTP), Secure Hypertext Transfer Protocol (HTTPS), Institute of Electrical and Electronics (IEEE) 802.11 protocol suite or other wireless protocols, and the like.

Figure 2:
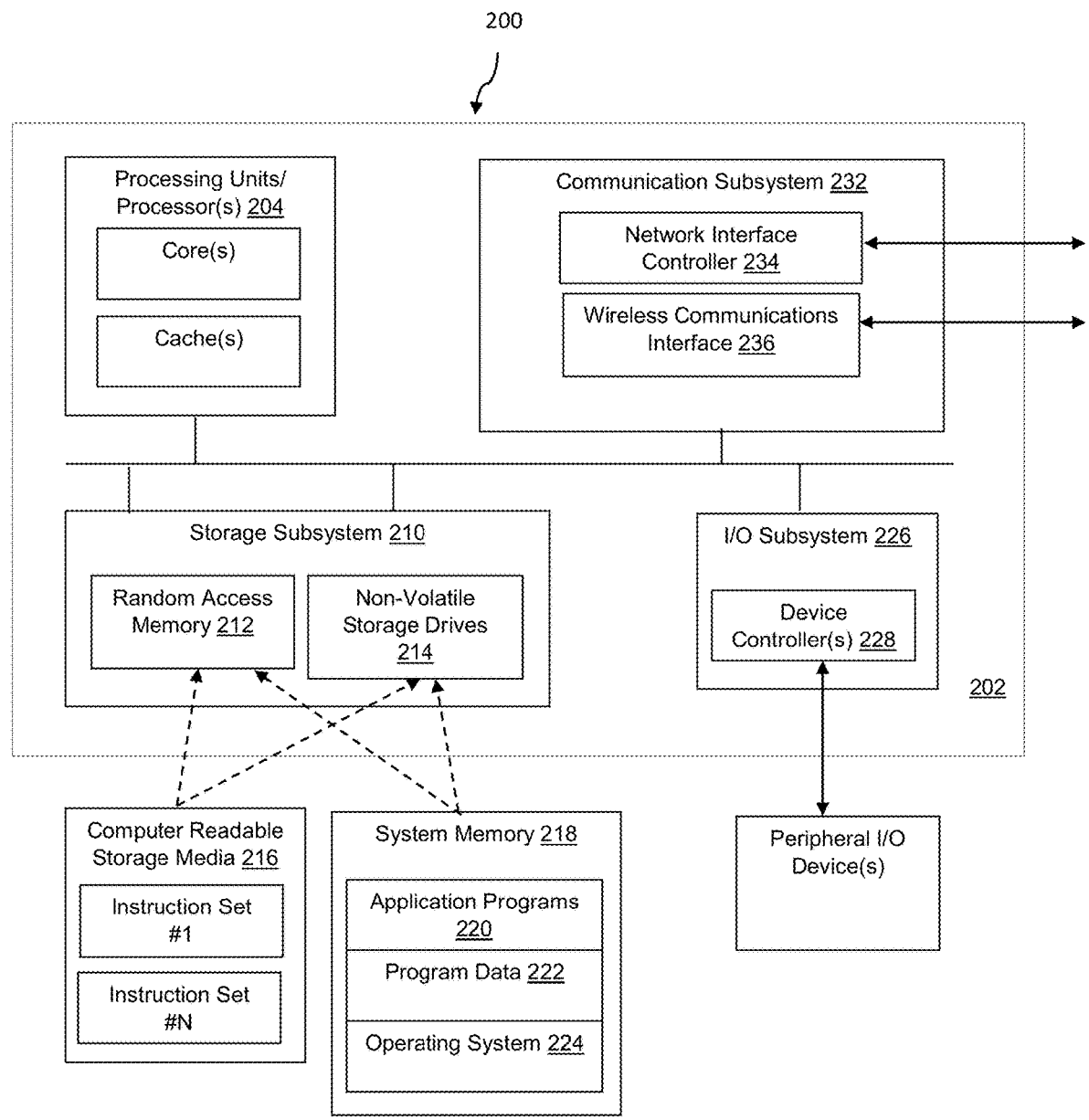
FIG. 2 illustrates a system level block diagram showing physical and logical components of a special-purpose computer device within a distributed computing environment, in accordance with an embodiment.

The embodiments shown in FIGS. 1-2 are thus one example of a distributed computing system and is not intended to be limiting. The subsystems and components within the server 102 and client devices 106 may be implemented in hardware, firmware, software, or combinations thereof. Various different subsystems and/or components 104 may be implemented on server 102. Users operating the client devices 106 may initiate one or more client applications to use services provided by these subsystems and components. Various different system configurations are possible in different distributed computing systems 100 and content distribution networks. Server 102 may be configured to run one or more server software applications or services, for example, web-based or cloud-based services, to support content distribution and interaction with client devices 106. Users operating client devices 106 may in turn utilize one or more client applications (e.g., virtual client applications) to interact with server 102 to utilize the services provided by these components. Client devices 106 may be configured to receive and execute client applications over one or more networks 120. Such client applications may be web browser based applications and/or standalone software applications, such as mobile device applications. Client devices 106 may receive client applications from server 102 or from other application providers (e.g., public or private application stores).

As shown in FIG. 1, various security and integration components 108 may be used to manage communications over network 120 (e.g., a file-based integration scheme or a service-based integration scheme). Security and integration components 108 may implement various security features for data transmission and storage, such as authenticating users or restricting access to unknown or unauthorized users, As non-limiting examples, these security components 108 may comprise dedicated hardware, specialized networking components, and/or software (e.g., web servers, authentication servers, firewalls, routers, gateways, load balancers, etc.) within one or more data centers in one or more physical location and/or operated by one or more entities, and/or may be operated within a cloud infrastructure.

In various implementations, security and integration components 108 may transmit data between the various devices in the content distribution network 100. Security and integration components 108 also may use secure data transmission protocols and/or encryption (e.g., File Transfer Protocol (FTP), Secure File Transfer Protocol (SFTP), and/or Pretty Good Privacy (PGP) encryption) for data transfers, etc.).

In some embodiments, the security and integration components 108 may implement one or more web services (e.g., cross-domain and/or cross-platform web services) within the content distribution network 100, and may be developed for enterprise use in accordance with various web service standards (e.g., the Web Service Interoperability (WS-I) guidelines). For example, some web services may provide secure connections, authentication, and/or confidentiality throughout the network using technologies such as SSL, TLS, HTTP, HTTPS, WS-Security standard (providing secure SOAP messages using XML encryption), etc. In other examples, the security and integration components 108 may include specialized hardware, network appliances, and the like (e.g., hardware-accelerated SSL and HTTPS), possibly installed and configured between servers 102 and other network components, for providing secure web services, thereby allowing any external devices to communicate directly with the specialized hardware, network appliances, etc.

Computing environment 100 also may include one or more data stores 110, possibly including and/or residing on one or more back-end servers 112, operating in one or more data centers in one or more physical locations, and communicating with one or more other devices within one or more networks 120. In some cases, one or more data stores 110 may reside on a non-transitory storage medium within the server 102. In certain embodiments, data stores 110 and back-end servers 112 may reside in a storage-area network (SAN). Access to the data stores may be limited or denied based on the processes, user credentials, and/or devices attempting to interact with the data store.

With reference now to FIG. 2, a block diagram of an illustrative computer system is shown. The system 200 may correspond to any of the computing devices or servers of the network 100, or any other computing devices described herein. In this example, computer system 200 includes processing units 204 that communicate with a number of peripheral subsystems via a bus subsystem 202. These peripheral subsystems include, for example, a storage subsystem 210, an I/O subsystem 226, and a communications subsystem 232.

One or more processing units 204 may be implemented as one or more integrated circuits (e.g., a conventional microprocessor or microcontroller), and controls the operation of computer system 200. These processors may include single core and/or multicore (e.g., quad core, hexa-core, octo-core, ten-core, etc.) processors and processor caches. These processors 204 may execute a variety of resident software processes embodied in program code, and may maintain multiple concurrently executing programs or processes. Processor(s) 204 may also include one or more specialized processors, (e.g., digital signal processors (DSPs), outboard, graphics application-specific, general purpose graphics processing units (GPGPUs), and/or other processors).

Bus subsystem 202 provides a mechanism for intended communication between the various components and subsystems of computer system 200. Although bus subsystem 202 is shown schematically as a single bus, alternative embodiments of the bus subsystem may utilize multiple buses. Bus subsystem 202 may include a memory bus, memory controller, peripheral bus, and/or local bus using any of a variety of bus architectures (e.g. Industry Standard Architecture (ISA), Micro Channel Architecture (MCA), Enhanced ISA (EISA), Video Electronics Standards Association (VESA), and/or Peripheral Component Interconnect (PCI) bus, possibly implemented as a Mezzanine bus manufactured to the IEEE P1386.1 standard).

I/O subsystem 226 may include device controllers 228 for one or more user interface input devices and/or user interface output devices, possibly integrated with the computer system 200 (e.g., integrated audio/video systems, and/or touchscreen displays), or may be separate peripheral devices which are attachable/detachable from the computer system 200. Input may include keyboard or mouse input, audio input (e.g., spoken commands), motion sensing, gesture recognition (e.g., eye gestures), etc.

As non-limiting examples, input devices may include a keyboard, pointing devices (e.g., mouse, trackball, and associated input), touchpads, touch screens, scroll wheels, click wheels, dials, buttons, switches, keypad, audio input devices, voice command recognition systems, microphones, three dimensional (3D) mice, joysticks, pointing sticks, gamepads, graphic tablets, speakers, digital cameras, digital camcorders, portable media players, webcams, image scanners, fingerprint scanners, barcode readers, 3D scanners, 3D printers, laser rangefinders, eye gaze tracking devices, medical imaging input devices, MIDI keyboards, digital musical instruments, and the like.

In general, use of the term "output device" is intended to include all possible types of devices and mechanisms for outputting information from computer system 200 to a user or other computer. For example, output devices may include one or more display subsystems and/or display devices that visually convey text, graphics and audio/video information (e.g., cathode ray tube (CRT) displays, flat-panel devices, liquid crystal display (LCD) or plasma display devices, projection devices, touch screens, etc.), and/or non-visual displays such as audio output devices, etc. As non-limiting examples, output devices may include, indicator lights, monitors, printers, speakers, headphones, automotive navigation systems, plotters, voice output devices, modems, etc.

Computer system 200 may comprise one or more storage subsystems 210, comprising hardware and software components used for storing data and program instructions, such as system memory 218 and computer-readable storage media 216.

System memory 218 and/or computer-readable storage media 216 may store program instructions that are loadable and executable on processor(s) 204. For example, system memory 218 may load and execute an operating system 224, program data 222, server applications, client applications 220, Internet browsers, mid-tier applications, etc.

System memory 218 may further store data generated during execution of these instructions. System memory 218 may be stored in volatile memory (e.g., random access memory (RAM) 212, including static random access memory (SRAM) or dynamic random access memory (DRAM)). RAM 212 may contain data and/or program modules that are immediately accessible to and/or operated and executed by processing units 204.

System memory 218 may also be stored in non-volatile storage drives 214 (e.g., read-only memory (ROM), flash memory, etc.) For example, a basic input/output system (BIOS), containing the basic routines that help to transfer information between elements within computer system 200 (e.g., during start-up) may typically be stored in the non-volatile storage drives 214.

Storage subsystem 210 also may include one or more tangible computer-readable storage media 216 for storing the basic programming and data constructs that provide the functionality of some embodiments. For example, storage subsystem 210 may include software, programs, code modules, instructions, etc., that may be executed by a processor 204, in order to provide the functionality described herein. Data generated from the executed software, programs, code, modules, or instructions may be stored within a data storage repository within storage subsystem 210.

Storage subsystem 210 may also include a computer-readable storage media reader connected to computer-readable storage media 216. Computer-readable storage media 216 may contain program code, or portions of program code. Together and, optionally, in combination with system memory 218, computer-readable storage media 216 may comprehensively represent remote, local, fixed, and/or removable storage devices plus storage media for temporarily and/or more permanently containing, storing, transmitting, and retrieving computer-readable information.

Computer-readable storage media 216 may include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 200.

By way of example, computer-readable storage media 216 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 216 may include, but is not limited to, Zip® drives, flash memory cards, universal serial bus (USB) flash drives, secure digital (SD) cards, DVD disks, digital video tape, and the like. Computer-readable storage media 216 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magneto-resistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 200.

Communications subsystem 232 may provide a communication interface from computer system 200 and external computing devices via one or more communication networks, including local area networks (LANs), wide area networks (WANs) (e.g., the Internet), and various wireless telecommunications networks. As illustrated in FIG. 2, the communications subsystem 232 may include, for example, one or more network interface controllers (NICs) 234, such as Ethernet cards, Asynchronous Transfer Mode NICs, Token Ring NICs, and the like, as well as one or more wireless communications interfaces 236, such as wireless network interface controllers (WNICs), wireless network adapters, and the like. Additionally and/or alternatively, the communications subsystem 232 may include one or more modems (telephone, satellite, cable, ISDN), synchronous or asynchronous digital subscriber line (DSL) units, Fire Wire® interfaces, USB® interfaces, and the like. Communications subsystem 236 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

In some embodiments, communications subsystem 232 may also receive input communication in the form of structured and/or unstructured data feeds, event streams, event updates, and the like, on behalf of one or more users who may use or access computer system 200. For example, communications subsystem 232 may be configured to receive data feeds in real-time from users of social networks and/or other communication services, web feeds such as Rich Site Summary (RSS) feeds, and/or real-time updates from one or more third party information sources (e.g., data aggregators). Additionally, communications subsystem 232 may be configured to receive data in the form of continuous data streams, which may include event streams of real-time events and/or event updates (e.g., sensor data applications, financial tickers, network performance measuring tools, clickstream analysis tools, automobile traffic monitoring, etc.). Communications subsystem 232 may output such structured and/or unstructured data feeds, event streams, event updates, and the like to one or more data stores that may be in communication with one or more streaming data source computers coupled to computer system 200.

The various physical components of the communications subsystem 232 may be detachable components coupled to the computer system 200 via a computer network, a FireWire® bus, or the like, and/or may be physically integrated onto a motherboard of the computer system 200. Communications subsystem 232 also may be implemented in whole or in part by software.

Due to the ever-changing nature of computers and networks, the description of computer system 200 depicted in the figure is intended only as a specific example. Many other configurations having more or fewer components than the system depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments.

Figure 3:
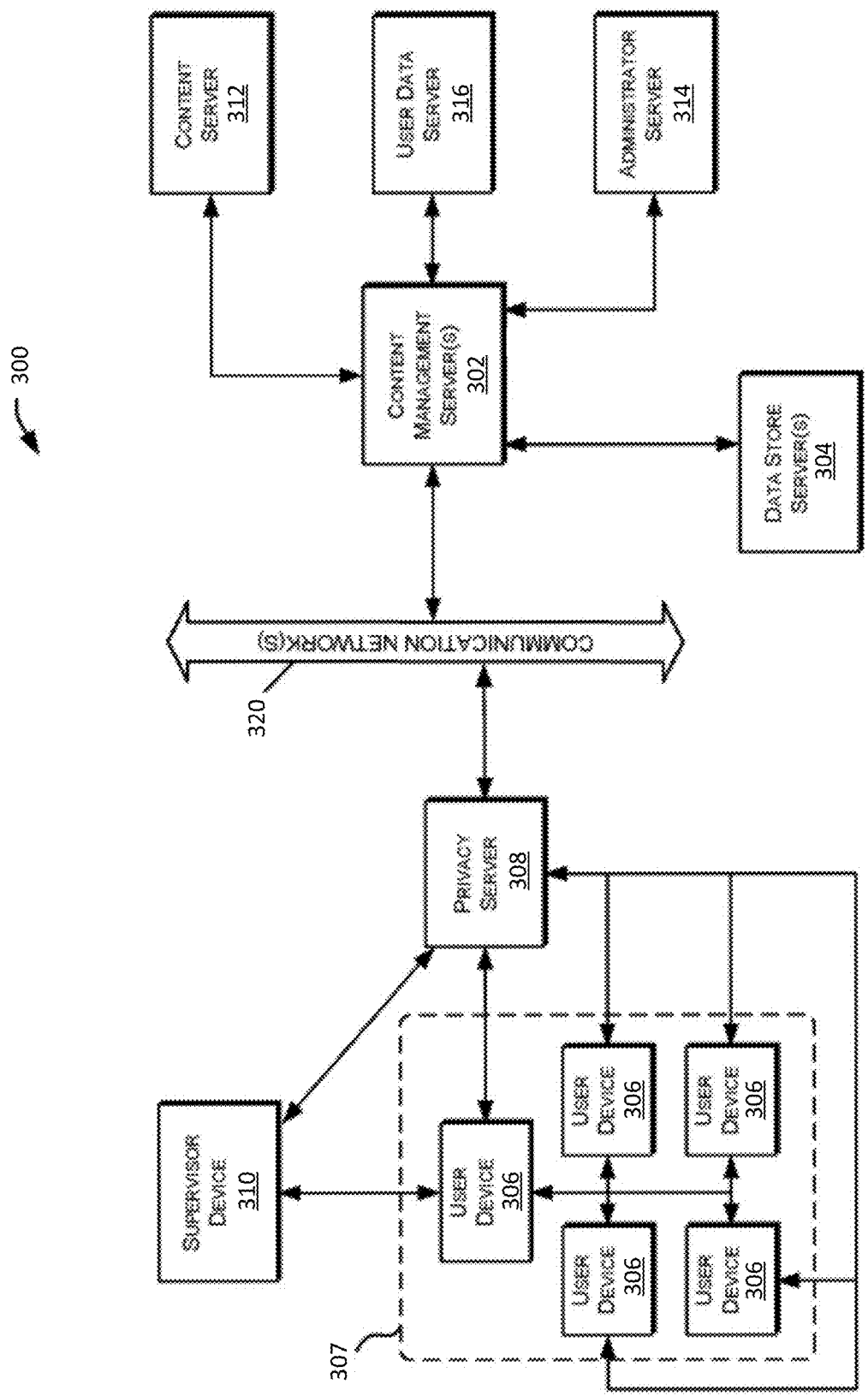
FIG. 3 illustrates a block diagram of an example content distribution network, in accordance with an embodiment.

With reference now to FIG. 3, a block diagram is shown illustrating various components of a content distribution network (CDN) 300 which implements and supports certain embodiments and features described herein. In some embodiments, the content distribution network 300 may include one or several physical components and/or one or several virtual components such as, for example, one or several cloud computing components. In some embodiments, the content distribution network 300 may include a mixture of physical and cloud computing components.

Content distribution network 300 may include one or more content management servers 302. Content management servers 302 may include any desired type of server including, for example, a rack server, a tower server, a miniature server, a blade server, a mini rack server, a mobile server, an ultra-dense server, a super server, or the like, and may include various hardware components, for example, a motherboard, a processing units, memory systems, hard drives, network interfaces, power supplies, etc. For example, the content management servers 302 may correspond to the computer server 102 of FIG. 1. Content management server 302 may include one or more server farms, clusters, or any other appropriate arrangement and/or combination or computer servers. Content management server 302 may act according to stored instructions located in a storage subsystem (e.g., storage subsystem 210 of FIG. 2) of the server 302, and may run an operating system, including any commercially available server operating system and/or any other operating systems discussed herein.

The content distribution network 300 may include one or more data store servers 304, such as database servers and file-based storage systems. The data store servers 304 can access data that can be stored on a variety of hardware components.

Data store servers 304 may comprise stored data relevant to the functions of the content distribution network 300. In some embodiments, multiple data stores may reside on a single server 304, either using the same storage components of server 304 or using different physical storage components to assure data security and integrity between data stores. In other embodiments, each data store may have a separate dedicated data store server 304.

Content distribution network 300 also may include one or more user devices 306 and/or supervisor devices 310. User devices 306 and supervisor devices 310 may display content received via the content distribution network 300, and may support various types of user interactions with the content. User devices 306 and supervisor devices 310 may include mobile devices such as smartphones, tablet computers, personal digital assistants, and wearable computing devices. Such mobile devices may run a variety of mobile operating systems, and may be enabled for Internet, e-mail, short message service (SMS), Bluetooth®, mobile radio-frequency identification (M-RFID), and/or other communication protocols. Other user devices 306 and supervisor devices 310 may be general purpose personal computers or special-purpose computing devices including, by way of example, personal computers, laptop computers, workstation computers, projection devices, and interactive room display systems. Additionally, user devices 306 and supervisor devices 310 may be any other electronic devices, such as a thin-client computers, an Internet-enabled gaming systems, business or home appliances, and/or a personal messaging devices, capable of communicating over network(s) 320.

In different contexts of content distribution networks 300, user devices 306 and supervisor devices 310 may correspond to different types of specialized devices, for example, student devices and teacher devices in an educational network, employee devices and presentation devices in a company network, different gaming devices in a gaming network, clinician/teacher devices and patient/student devices in a clinical diagnosis or learning classification network, etc. Additionally, different user devices 306 and supervisor devices 310 may be assigned different designated roles, such as presenter devices, teacher devices, clinician devices, administrator devices, or the like, and in such cases the different devices may be provided with additional hardware and/or software components to provide content and support user capabilities not available to the other devices.

The content distribution network 300 also may include a privacy server 308 that maintains private user information at the privacy server 308 while using applications or services hosted on other servers. For example, the privacy server 308 may be used to maintain private data of a user within one jurisdiction even though the user is accessing an application hosted on a server (e.g., the content management server 302) located outside the jurisdiction. In such cases, the privacy server 308 may intercept communications between a user device 306 or supervisor device 310 and other devices that include private user information. The privacy server 308 may create a token or identifier that does not disclose the private information and may use the token or identifier when communicating with the other servers and systems, instead of using the user's private information.

The content distribution network 300 may include one or more communication networks 320. Although only a single network 320 is identified in FIG. 3, the content distribution network 300 may include any number of different communication networks between any of the computer servers and devices shown in FIG. 3 and/or other devices described herein. Communication networks 320 may enable communication between the various computing devices, servers, and other components of the content distribution network 300. Various implementations of content distribution networks 300 may employ different types of networks 320, for example, computer networks, telecommunications networks, wireless networks, and/or any combination of these and/or other networks.

As illustrated in FIG. 3, the content management server 302 may be in communication with one or more additional servers, such as a content server 312, an administrator server 314, and/or a user data server 316. Each of these servers may include some or all of the same physical and logical components as the content management server(s) 302, and in some cases, the hardware and software components of these servers 312-316 may be incorporated into the content management server(s) 302, rather than being implemented as separate computer servers.

Content server 312 may include hardware and software components to generate, store, and maintain the content resources for distribution to user devices 306 and other devices in the network 300. For example, in content distribution networks 300 used for professional training and educational purposes, or clinical diagnosis of students/patents, the content server 312 may include data stores of training materials, presentations, plans, syllabi, reviews, evaluations, interactive programs and simulations, course models, course outlines, assessments and diagnostic modules, and various training interfaces that correspond to different materials and/or different types of user devices 306.

Administrator server 314 may include hardware and software components to initiate various administrative functions at the content management server 302 and other components within the content distribution network 300. For example, the administrator server 314 may monitor device status and performance for the various servers, data stores, and/or user devices 306 in the content distribution network 300. When necessary, the administrator server 314 may add or remove devices from the network 300, and perform device maintenance such as providing software updates to the devices in the network 300. Various administrative tools on the administrator server 314 may allow authorized users to set user access permissions to various content resources, monitor resource usage by users and devices 306, and perform analyses and generate reports on specific network users and/or devices (e.g., resource usage tracking reports, training evaluations, etc.).

User data server 316 may include hardware and software components that store and process data for multiple users relating to each user's activities and usage of the content distribution network 300. For example, the content management server 302 may record and track each user's system usage, including their user device 306, content resources accessed, and interactions with other user devices 306. This data may be stored and processed by the user data server 316, to support user tracking and analysis features. For instance, in the contexts of professional training, education, and/or clinical diagnosis of students or patients, the user data server 316 may store and analyze assessment item parts of assessment items of digital assessments completed by each user or training materials viewed, presentations attended, courses or tests completed, the user's responses to assessment item parts of the assessment items or other interactions, assessment item part, or evaluation results, and the like. Individual assessment items may be included as part of a title, which may correspond to a particular course or textbook (e.g., digital course or digital textbook) for a particular subject. A title may include multiple assessment items, which may be organized into sections, which may be organized into chapters. Each assessment item may include one or more assessment item parts to which users may interact with and submit responses to. In some embodiments, a teacher may group together multiple assessment items into a digital assessment (e.g., corresponding to a homework assignment, a test, a quiz, an activity, or another applicable type of assessment).

For example, when a user (sometimes referred to herein in this context as a responder) completely or partially completes an assessment item, the responses to each of the assessment item parts of the assessment item that are responded to by the user may be stored in the user data server 316 (e.g., as response data). It should be understood that the methods described herein by which response data and corresponding user and assessment item identifier information are stored are intended to be illustrative and not limiting. If desired, alternative organizational data storage paradigms may be used. As used herein, an "assessment item part" refers to the smallest measurable part of any activity with built-in assessment (e.g., activities such as a tutorial, a formative, summative, or diagnostic test or quiz, or any other applicable activity). Assessment item parts may include, for example, selected response items (e.g., multiple-choice or true-or-false questions), and/or constructed response items (e.g., fill in the blank questions). The user data server 316 may then analyze the responses and generate grades for the responses corresponding to whether each response is correct (in which case a grade of "1" is generated) or incorrect (in which case a grade of "0" is generated). The generated grades may be stored in the data server 316. In some embodiments, assessment items may provide a user with the option of accessing a hint before responding to the assessment item part. For each response stored in the data server 316, a corresponding hint usage value may also be stored (e.g., in a corresponding data entry), which may be used to indicate whether the user accessed a hint before responding to the corresponding assessment item part. For example, a hint usage value of 1 indicates that a hint was accessed by the user when responding to the corresponding assessment item part, while a hint usage value of 0 indicates that a hint was not accessed.

In some embodiments, the data store servers 304 may store assessment data corresponding to one or more assessment item parts of one or more assessment items of one or more titles. For a given assessment item, a corresponding subset of the assessment data stored in the data store servers 304 may include responses, grades, hint usage values, and responder (i.e., user) information (e.g., including user identifiers) for each assessment item part of that assessment item. For example, the portion of the assessment data corresponding to a given assessment item part (which may sometimes be referred to as the assessment item part data for that assessment item part) may include a dataset (e.g., a look-up table (LUT)) of responders that have responded to the assessment item part. Each entry of the dataset may correspond to a different responder and may include the user ID of the responder, an assessment item identifier from which the assessment item, assessment, section, chapter, and title of the corresponding assessment item may be determined, a grade for the response (e.g., 1 for a correct answer and 0 for an incorrect answer), and a hint usage value for the response (e.g., 1 if a hint was used and 0 if a hint was not used). As will now be described, the assessment data stored in the data store servers 304 may be used as a basis for estimating the latent abilities of users represented in the assessment data, and for estimating the quality of assessment item parts of assessment items included in the title corresponding to the assessment data using, for example, an item response theory (IRT) model and maximum likelihood estimation (MLE).

IRT is a technique for evaluating the latent abilities of responders (e.g., which may be quantified as individual ability values) to a group of assessment items (e.g., of a title) through their performance on assessment item parts of those assessment items. The IRT model allows the quality of each assessment item part of an assessment item to be individually evaluated and quantified. For example, if responders tend to perform poorly on an assessment item part that was intended by its authors to be easy, then the assessment item part may be too difficult and should be redesigned.

In an embodiment, a two-parameter logistic item response (2PL IRT) model may be used to estimate assessment item part parameters. The basic 2PL IRT model estimates the values of two parameters (i.e., properties) of an assessment item part. For example, the 2PL IRT model may be used to estimate the difficulty and discrimination (e.g., which may be quantified by a difficulty value and a discrimination value, respectively) of each assessment item part of a title. In some embodiments, a modified 2PL model may be used, which, in addition to estimating assessment item part difficulty and discrimination values, may estimate a hint change value that is indicative of the impact that using hints has on the probability of a responder submitting a correct first response to the assessment item part. In addition to user/responder identifiers, assessment item part identifiers, and grades, the modified 2PL IRT model may also take hint usage values as inputs, which may indicate whether a particular responder used a hint before responding to the assessment item part. An example modified 2PL IRT model may take the following form:

$$P(Y=1) = \frac{1}{1+\exp(-\eta)} \quad \text{(Eq. 1)}$$

$$\eta = D_1 \cdot A - D_2 - hint_{change} \cdot hint_{usage} \quad \text{(Eq. 2)}$$

where $P(Y=1)$ is the probability of a responder correctly responding to the assessment item part on their first attempt (sometimes referred to herein as the correct first response probability value), $D_1$ is the discrimination value of the assessment item part, $A$ is the ability value of the responder, $D_2$ is the difficulty value of the assessment item part, $hint_{change}$ is the hint change value indicating an expected shift in difficulty of the assessment item part expected as a result of the responder using a hint before responding to the assessment item part, and $hint_{usage}$ is the hint usage value with a hint usage value of 1 indicating that a hint was used by the responder and a hint usage value of 0 indicating that a hint was not used by the responder. It should be noted that a positive hint change value indicates that the use of a hint decreases the chance of a correct response, hint change value of zero indicates that the use of a hint has no influence on the chance of a correct response, and negative hint change value means the hint increases the chance of a correct response. As will be described, optimization (e.g., using MLE via a gradient descent optimization algorithm) based on the modified 2PL IRT model of Eqs. 1 and 2 may be performed by one or more processors (e.g., processors 204 of FIG. 2, which may include one or more general purpose graphics processing units) of one or more computer systems (e.g., computer system 200 of FIG. 2) based on assessment data collected from a sample population of responders in order to determine the difficulty value, the discrimination value, and the hint change value of each assessment item part of a title, and to generate ability values for each responder of the sample population. It should be noted that the sample population of responders may be limited to responders and corresponding response data and/or assessment data for a single title. Assessment data for different titles may have different sample populations of responders.

Figure 7:
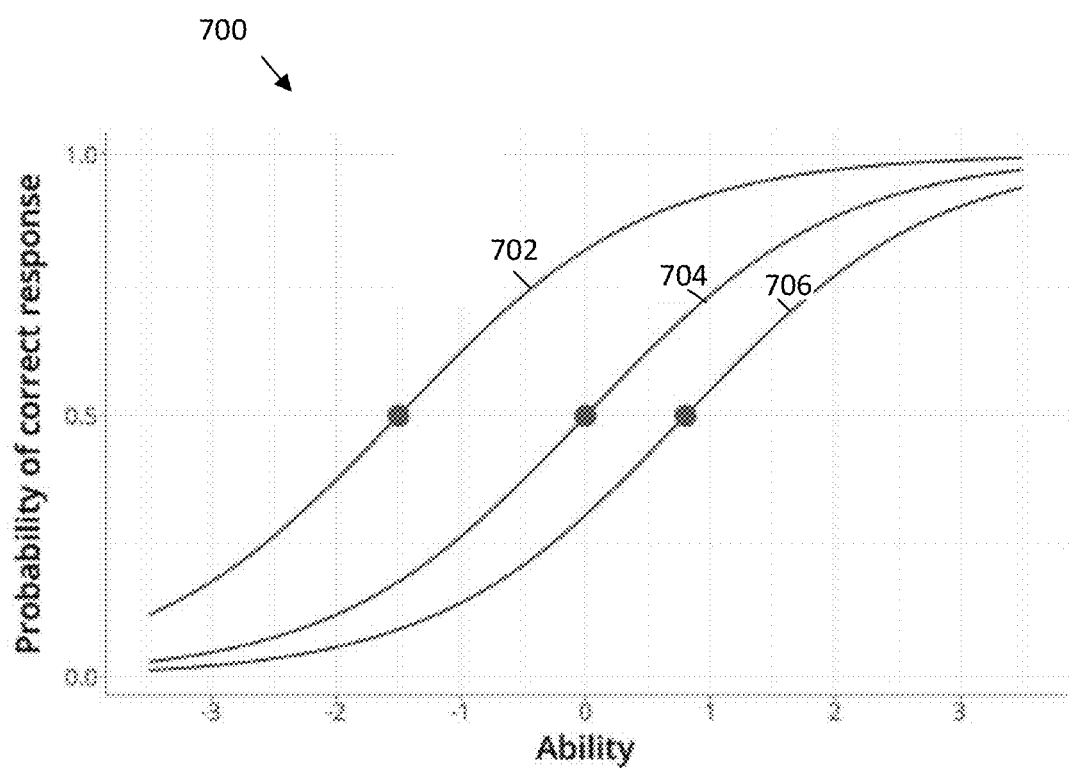
FIG. 7 illustrates a chart showing three different item characteristic curves, each corresponding to different levels of assessment item part difficulty, in accordance with an embodiment.

As used herein, the difficulty value for an assessment item part is quantified as the ability value at which a responder is estimated to have a 50% probability of answering the assessment item part correctly on their first attempt (i.e., the initial correct response probability for the responder with respect to the assessment item part). For example, a difficulty value of 0 indicates that a responder having an ability value of 0 is estimated to have a 50% chance of responding correctly to the assessment item part. An assessment item part with a difficulty value of 1 is considered to be more difficult than an assessment item part with a difficulty value of 0. An assessment item part with a difficulty value of −1 is considered to be less difficult than an assessment item part with a difficulty value of 0. FIG. 7 shows a chart 700 of responder ability value vs. the probability of a correct response be selected by the responder on their first attempt. The chart 700 includes item characteristic curves 702, 704, and 706 representing three assessment item parts having different difficulties values. Item characteristic curves referred to herein are used to show the estimated probability of a responder answering an assessment item part correctly on their first attempt, given the ability value of the responder, and are a visual representation of an IRT model that has been determined for the assessment item part, as will be described. As shown, the curve 702 has a difficulty value of around −1.5, the curve 704 has a difficulty value of around 0, and the curve 706 has a difficulty value of about 0.8. Comparatively, this indicates that the assessment item part represented by the curve 702 is estimated to be less difficult than both assessment item parts represented by the curves 704 and 706, and that the assessment item part represented by the curve 704 is estimated to be less difficult than the assessment item part represented by the curve 706.

Figure 8:
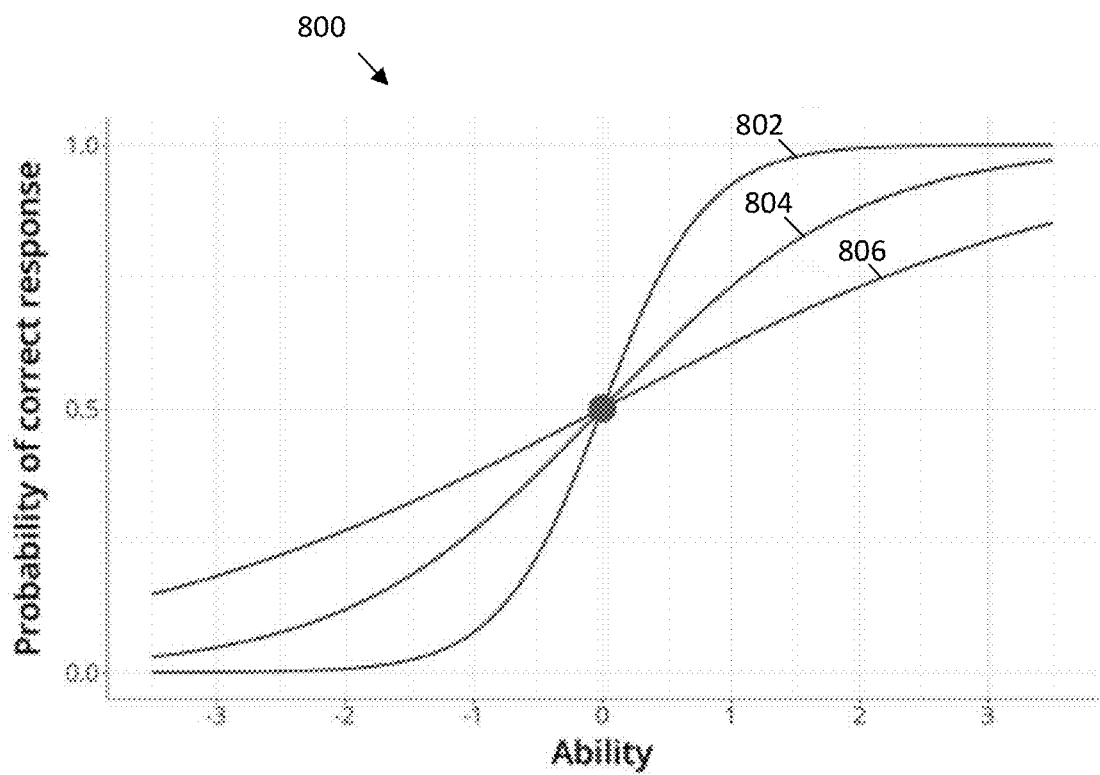
FIG. 8 illustrates a chart showing three different item characteristic curves, each corresponding to different levels of assessment item part discrimination, in accordance with an embodiment.

As used herein, the discrimination value for an assessment item part describes how well the assessment item part can differentiate between responders having different ability values. For example, the discrimination value of a given assessment item part may be quantified as the local rate of change of a corresponding item characteristic curve at a midpoint of the item characteristic curve (e.g., corresponding to a 50% probability of a responder providing a correct response to the assessment item part on their first attempt). A lower discrimination value may indicate that the assessment item part is less likely to discriminate between learners of different ability levels compared to a desired (e.g., predetermined rate). As shown in FIG. 8, a chart 800 includes item characteristic curves 802, 804, and 806. Curve 802 corresponds to an assessment item part having a relatively high discrimination value, as the probability of responding correctly to that assessment item part increases rapidly (e.g., the curve has a relatively high rate of change) as responder ability increases. For example, learners with an ability value of −1 have a much lower estimated probability of responding to the assessment item part represented by the curve 802 correctly (about 10%) compared to that of learners with an ability value of 1 (about 90%). Curve 804 corresponds to an assessment item part having a relatively moderate discrimination value. Curve 806 corresponds to an assessment item part having a relatively low discrimination value, with the relationship between ability and the probability of responding correctly to the assessment item part being flatter (e.g., having a smaller positive rate of change) around the midpoint of the item characteristic curve. For example, learners with an ability value of −1 have a similar estimated probability of responding to the assessment item part represented by the curve 806 correctly (about 40%) compared to that of learners with an ability value of 1 (about 60%).

The process of estimating responders' latent ability and estimating IRT model parameters for assessment item parts of an assessment item of a given title, as described above, may be managed via a workflow manager module executed by a processor of one or more of the data store servers 304.

Figure 4:
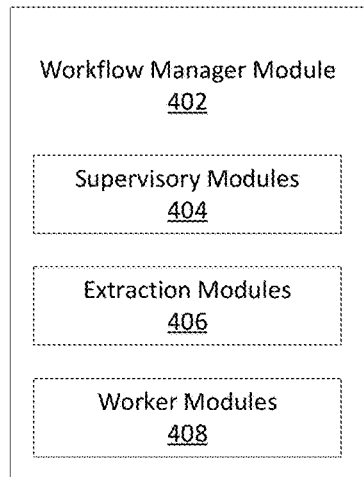
FIG. 4 illustrates a workflow manager module that may be executed by a processor of a computer device within a distributed computing environment, in accordance with an embodiment.

FIG. 4 shows a workflow manager module 402 that may be executed by one or more processors (e.g., processors 204 of FIG. 2) of one or more computer systems (e.g., servers 102, 112, 304 FIGS. 1, 3), and that manages the process of estimating IRT model parameters for assessment items of a title. The workflow manager module 402 may include supervisory modules 404, extraction modules 406, and worker modules 408. A computer system that includes a processor that executes at least a portion of the workflow manager module 402 may be referred to as a workflow manager server.

The supervisory modules 404 supervise the entire processing workflow when processing assessment data for assessment items of a title to determine ability values of responders and assessment item part parameters for the modified 2PL IRT model. For example, the supervisory modules 404 may control the execution the worker modules 408, as needed. The supervisory modules 404 may also automatically initiate general process graphics processing unit (GPGPU) instances that may be used to process the assessment data, as needed, and may automatically stop GPGPU instances once modelling has ended. These GPGPU instances may, for example, be implemented using one or more physical graphics processing units (GPUs) (e.g., GPGPUs of the processing units 204 of FIG. 2). In some embodiments, these physical GPUs may be system components (e.g., system components 104 of FIG. 1) of one or more data center servers (e.g., servers 102 of FIG. 1). The computer systems executing the workflow manager module 402 may include these data center servers or may be connected to these data center servers via one or more communications networks (e.g., communications networks 120, 320, FIGS. 1, 3).

Figure 5:
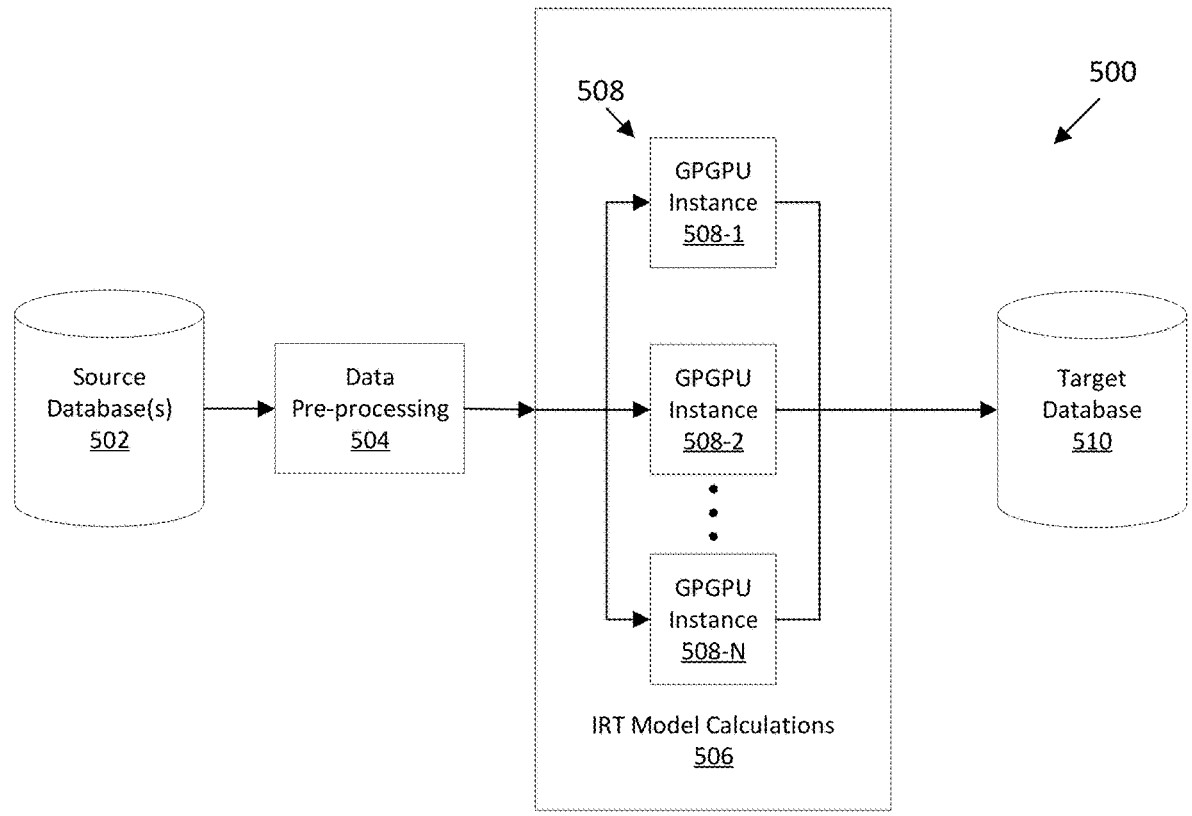
FIG. 5 illustrates a conceptual block diagram showing the flow of data during IRT modelling of assessment data corresponding to assessment item parts of assessment items of a title, in accordance with an embodiment.

The extraction modules 406 may be controlled by the workflow manager 402 and may extract assessment data corresponding to the assessment items of a title from one or more source databases (e.g., source database 502 of FIG. 5). The source databases may, for example, be stored on one or more computer memory devices of one or more source data store servers (e.g., data store servers 304 of FIG. 3), which may be connected in electronic communication with the server or servers that include the processor or processors executing the workflow manager module 402 via one or more electronic communication networks (e.g., communication networks 120, 320, FIGS. 1, 3). The extraction modules 406 may pre-process the assessment data to transform the assessment data into a desired format, filter out unwanted data points, and separate the assessment data into batches for parallel processing, for example. For example, assessment data that has been pre-processed in preparation for IRT modelling may include only response data that includes responders' first attempts at responding to assessment item parts of assessment items of the corresponding title.

The worker modules 408 may apply dataflow programming methods running on the GPGPU instances initiated by the supervisory modules 404 to estimate responder ability values and estimate assessment item part parameter values (e.g., difficulty value, discrimination value and hint change value) according to a modified 2PL IRT model for each assessment item part of the assessment items of the title, and may cause the estimated ability values and estimated assessment item part parameters to be stored in one or more target databases (e.g., target database 510 of FIG. 5). In an embodiment, the estimated ability values may be stored in a different database from the database in which the estimated assessment item part parameters are stored. In some embodiments, each GPGPU instance may process a separate batch of the pre-processed assessment data (e.g., with each batch of assessment data corresponding to a different individual title), as defined during pre-processing by the extraction modules 406 so that the assessment data of multiple titles may be processed and modelled in parallel. The target databases may, for example, be stored on one or more computer memory devices of one or more target data store servers (e.g., data store servers 304 of FIG. 3), which may be connected in electronic communication with the server or servers that include the processor or processors executing the workflow manager module 402 via one or more electronic communication networks (e.g., communication networks 120, 320, FIGS. 1, 3).

FIG. 5 shows a block diagram illustrating dataflow architecture 500 of assessment data for a title that undergoes processing (including IRT modelling) to determine assessment item parameters for each assessment item part of the assessment items of the title. Some aspects of the dataflow architecture 500 will be described in the context of the workflow manager module 402 of FIG. 4. One or more source databases 502 (e.g., stored on one or more computer memory devices of one or more source data store servers of the data store servers 304, FIG. 3) may store assessment data corresponding to a title. The source database(s) 502 may be in electronic communication with the computer system(s) executing the workflow manager module 402 via one or more communications networks (e.g., communication networks 120, 320, FIGS. 1, 3).

The assessment data may include multiple entries. Each entry may include, a user identifier that identifies the responder that submitted a response corresponding to that entry, an assessment item part identifier that identifies the assessment item part corresponding to that entry, a grade for the response submitted by the responder (e.g., 1 if the response is correct and 0 if the response is incorrect), and a hint usage value. For example, the assessment item part identifier may allow the title, chapter, section, assessment item, and assessment item part corresponding to a given entry to be identified. The assessment data may include entries corresponding to multiple titles, each including multiple assessment items and assessment item parts. The extraction modules 406 may retrieve the assessment data from the source database(s) 502 (e.g., in response to instructions received from the supervisory modules 404) before proceeding to a data pre-processing block 504.

At the data pre-processing block 504, the extraction modules 406 may transform the assessment data into a desired format, filter unwanted data points out of the assessment data, and/or divide the assessment data into batches for parallel processing, for example. In some embodiments the dataset entries for responders who were "test users" (e.g., corresponding to a test user account that is not associated with an actual student) or responses from instructor/teacher user accounts are omitted from the pre-processed assessment data used in the IRT modelling, as such data may cause inaccuracy in estimation. Assessment item parts from titles that have a number of unique responders that do not exceed a predetermined threshold may be omitted from the pre-processed assessment data (e.g., as a large responder sample size may generally be desirable for accuracy of item parameter estimation). Additionally, all assessment data that does not correspond to responders' first attempts at responding to the corresponding assessment item part may be omitted from the pre-processed assessment data prior to IRT modelling. In this way, difficulty and discrimination values will be estimated based only on responders' first attempts.

As with the assessment data initially retrieved from the source database(s) 502, the pre-processed assessment data may include multiple entries, each entry including a user identifier, an assessment item part identifier, a grade, and a hint usage value. In some embodiments, each entry of the pre-processed assessment data may also include an indicator for whether a hint is available for the assessment item part corresponding to that entry. The pre-processed assessment data may be separated into batches, with each batch including a dataset corresponding to a particular title that may include multiple assessment items, each having one or more assessment item parts. Each batch of pre-processed assessment data may undergo IRT modelling separately at block 506 (e.g., may be processed by a different one of GPGPU instances 508).

At IRT model calculation block 506, the worker modules 408 may operate on the pre-processed assessment data using GPGPU instances 508 to estimate item parameter values (e.g., difficulty values, discrimination values, and hint change values) for each assessment item part represented in the pre-processed assessment data and to estimate ability values for each responder represented in the pre-processed assessment data based on a modified 2PL IRT model (e.g., according to Eqs. 1 and 2). It should be understood that IRT model calculation may be performed on a title-by-title basis, with each worker module 408 and GPGPU instance 508 generating estimated item parameters and estimated ability scores corresponding to only one respective title at any given time. For example, the worker modules 408 may use dataflow programming methods/paradigms (e.g., using an application programming interface such as TensorFlow) and perform MLE for the 2PL IRT model using respective subsets of the pre-processed assessment data corresponding to each assessment item part. In some embodiments the block 506, when performing MLE for a given assessment item part, may take the grade of each response, the user identifier of each responder, and the hint usage values as inputs, and may output a difficulty value, a discrimination value and hint change value for the assessment item part and ability values for each responder represented in the portion of the pre-processed assessment data that corresponds to the assessment item part. The outputs may maximize the likelihood function of the modified 2PL IRT Model and may attempt to minimize the loss function, as will be described. Calculations related to the performance of MLE for multiple batches of assessment data, each batch corresponding to a respectively different individual title may be processed in parallel using the GPGPU instances 508, which may be initiated by the supervisory modules 404.

In an embodiment, at block 506 a gradient descent optimization algorithm (e.g., the Adaptive Moment Estimation (Adam) optimizer) may be used in combination with a loss function to perform MLE to estimate the item parameters of each assessment item part. The gradient descent optimization algorithm may be iteratively performed to repeatedly estimate the item parameters to minimize the loss function (e.g., until a predetermined number of iterations have been determined or until the change in the output of the loss function for successive iterations is determined to have fallen below a predetermined threshold). For example, the loss function may be the sum of a cross entropy component, an ability mean component, and an ability standard deviation component. The cross entropy component may be a cross entropy loss between observed grades (e.g., corresponding grades of the pre-processed assessment data) and correct first response probability values calculated based on the estimated item parameter values (sometimes referred to herein as a cross entropy component). The ability mean component may be the absolute value of the mean estimated ability value for all responders represented in the pre-processed assessment data for a corresponding title. The ability standard deviation component may be the absolute value of the standard deviation of the ability value for all responders represented in the pre-processed assessment data for the corresponding title minus one. In some embodiments, the ability mean loss component and the ability standard deviation loss component may each be multiplied by a fractional value (e.g., 0.01) so that the weights of the ability mean loss and ability standard deviation loss components of the loss function are less than that of the cross-entropy component. In order to initially estimate the correct first response probability, initial estimated item parameters (e.g., difficulty value, discrimination value, hint change value) of each assessment item part may be randomly chosen from normal distributions, and may be subsequently updated via the iterative verification of the estimated item parameters and application of the loss function.

Once the difficulty value, discrimination value and hint change value for each assessment item part of assessment items of titles being processed have been estimated and verified at block 506, the worker modules 408 may output these estimated item parameters in a target database 510 (e.g., stored on one or more computer memory devices of one or more target data store servers of the data store servers 304, FIG. 3). The estimated ability values for the responders that submitted responses to the assessment item parts of assessment items of each title may be stored in one or more separate databases. The server or servers in which the target database(s) 510 are stored may be in electronic communication with the computer system(s) executing the workflow manager module 402 via one or more communications networks (e.g., communication networks 120, 320, FIGS. 1, 3).

Figure 6:
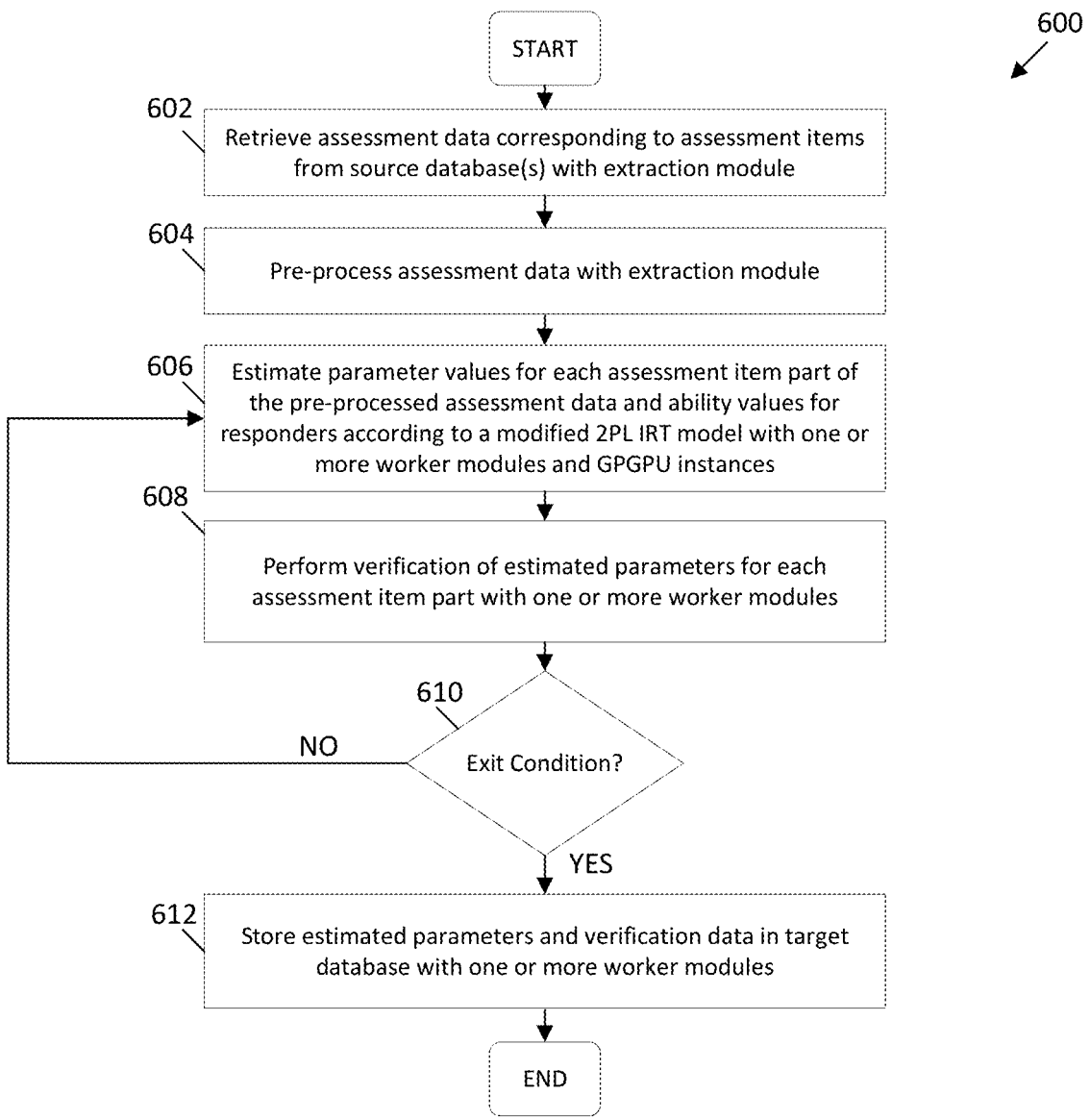
FIG. 6 illustrates a process flow diagram for a method of collecting assessment data, generating item parameter data for the assessment data based on an IRT model, and storing the item parameter data using dataflow programming methods, in accordance with an embodiment.

FIG. 6 shows an illustrative process flow for a method 600 by which assessment item part parameters may be determined for assessment items of one or more titles based on the modified 2PL IRT model (e.g., according Eqs. 1 and 2). For example, the method 600 may be performed in connection with the data flow architecture of FIG. 5. For example, the steps of the method 600 may be performed by executing computer-readable instructions stored in one or more system memories (e.g., system memory 218, FIG. 2) and/or computer-readable storage media (e.g., computer-readable storage media 216, FIG. 2) using one or more computer processors (e.g., processing units 204, FIG. 2) of one or more computer systems (e.g., computer system 200, FIG. 2).

At step 602, an extraction module (e.g., extraction module 404 of FIG. 404) may retrieve assessment data corresponding to a title from one or more source databases (e.g., source database 502).

At step 604, the extraction module may pre-process the assessment data to transform the assessment data into a desired format, filter out unwanted data points, and/or divide the assessment data into batches for parallel processing to produce pre-processed assessment data.

At step 606, one or more worker scripts and GPGPU instances may estimate item parameter values for each assessment item part of the pre-processed assessment data and estimate ability values for each responder represented in the pre-processed assessment data according to a modified 2PL IRT model (e.g., according to Eqs. 1 and 2) based on a the pre-processed assessment data. For example, a gradient descent optimization algorithm and loss function may be used (e.g., as described in detail in connection with block 506 of FIG. 5) to estimate the parameters (e.g., assessment item part parameters) of each assessment item part. The estimated item parameters may include a difficulty value, a discrimination value, and a hint change value for each assessment item part of the pre-processed assessment data, respectively. Of the estimated ability values determined at step 606, the estimated ability value for a given one the responders may correspond to an estimated latent ability of that responder with respect to a particular title.

By using multiple GPGPU instances operating in parallel to perform MLE for multiple titles (e.g., which may correspond to millions of assessment data entries in some cases), the amount of time required to complete IRT modelling and MLE may be significantly reduced compared to if the process were performed using a single central processing unit (CPU). For example, a set of assessment data that would take around 13 hours to process with a single CPU may only take around 40 minutes when processed with a single GPGPU instance. When processed with multiple GPGPU instances process the assessment data in parallel, the processing time required may decrease according to the number of GPGPU instances used. In an embodiment, each GPGPU instance may estimate item parameters for assessment item parts of a respectively different individual title (e.g., such that a single GPGPU does not processes assessment data corresponding to multiple titles).

At step 608, the estimated item parameter values produced at step 606 may undergo verification. For example, for a given assessment item part, the estimated assessment item part parameters and estimated ability values for each responder produced at step 606 may be input for their corresponding variables of the modified 2PL IRT model, from which a set of correct first response probability values may be calculated. Each correct first response probability value of the set may correspond to a different pre-processed assessment data entry that corresponds to the given assessment item part (e.g., such that each respective correct first responder probability value of the set corresponds to a different observed grade corresponding to the given assessment item part).

For each correct first response probability value of the set, a cross entropy loss may be calculated between that correct first response probability value (e.g., a value between 0 and 1) and the observed grade (e.g., a value of 0 for an incorrect response or a value of 1 for a correct response) of the corresponding entry. Different baselines (e.g., cross entropy loss baselines) may be established by calculating cross entropy loss between each individual observed grade that corresponds to the given assessment item part and: the average of the observed grades for the given assessment item part, the average of the observed grades for all assessment item parts of an entire title, and/or a value of 0.5.

Additionally or alternatively, for each correct first response probability value of the set, a mean squared error may be calculated between that correct first response probability value (e.g., a value between 0 and 1) and the observed grade (e.g., a value of 0 for an incorrect response or a value of 1 for a correct response) of the corresponding entry.

Different baselines (e.g., mean squared error baselines) may be established by calculating mean squared error between each individual observed grade that corresponds to the given assessment item part and: the average of the observed grades for the given assessment item part, the average of the observed grades for all assessment item parts of an entire title, and/or a value of 0.5.

Cross entropy losses, cross entropy loss baselines, mean squared errors, and mean squared error baselines may be aggregated at the assessment item part level, at the bin level, and at the title level. In some embodiments, the estimated item parameters may be considered a "good fit" when the cross entropy losses and/or mean square errors at a given level of aggregation are less than the corresponding cross entropy loss baselines and mean squared error baselines at that level of aggregation, respectively.

Aggregation at the bin level may be performed by grouping the set of correct first response probability values into a number of bins (e.g., 20 bins) of equal width, determining an average of the correct first response probability values for each respective bin (e.g., to produce estimated average bin values), and determining an average observed grade for each respective bin (e.g., to produce observed average bin values).

In some embodiments, the estimated item parameters may be considered a "good fit" when the cross entropy losses and/or mean square errors are less than the corresponding cross entropy loss baselines and mean squared error baselines, respectively, for each bin. In some embodiments, the estimated item parameters may be considered a "good fit" if a difference between the average correct first response probability and the average observed grade for each bin is below a predetermined threshold (i.e., the average correct first response probability and the average observed grade for each bin are sufficiently close in value). In another embodiment, a "good fit" may be defined as the value of each bin being between boundaries of the bin. For example, when considering a bin with boundaries between 0.55 and 0.6, the average observed grade equals 0.57, this is considered a "good fit." In some embodiments, cross entropy and/or mean squared error may be calculated for each bin and then aggregated to obtain a single cross entropy loss value and/or a single mean squared error value for a title. This aggregation may take into account the different number of observations in each bin.

All verification metrics calculated at step 608 (e.g., including average observed grades, average correct first response probability values, average cross entropy loss and/or mean squared error values, and average cross entropy loss and/or mean squared error baselines) may be stored in the target database with one or more worker modules.

At step 610, the method 600 determines whether an exit condition has occurred. For example, an exit condition may occur when the number of iterations of steps 606 through 610 that have been performed exceeds a predetermined threshold. As another example, an exit condition may occur when the cross entropy losses and/or mean squared errors at different levels of aggregation calculated at step 606 remain substantially unchanged (e.g., having changed by less than a predetermined threshold) between multiple consecutive iterations of steps 606-610. As another example, an exit condition may occur when the estimated item parameters are verified as being a "good fit," at step 608 (e.g., when the cross entropy losses and/or mean squared errors at different levels of aggregation calculated at step 608 are within a predefined acceptable range of values). If an exit condition has not occurred, the method 600 proceeds to step 612. Otherwise, the method 600 returns to step 606 and the assessment item part parameter values of each assessment item part are estimated again.

At step 612, the worker modules may cause the estimated item parameter values for each assessment item part to be stored in at least one target database (e.g., target database 510, FIG. 5) of at least one server that is in communication with the one or more computer systems executing the method 600. In some embodiments, the estimated item parameters produced each iteration of step 606 may be stored in the at least one target database. Additionally, verification data (e.g., including the average bin difference value, the average cross entropy loss value, and/or the mean squared errors) and responder ability data (e.g., including estimated ability values of all responders) may be stored in separate databases of one or more servers, which may include the server or servers on which the estimated item parameter values are stored. It should be understood that while estimated item parameter values and verification data are shown here to be stored in the at least one target database after step 610, in other embodiments, the estimated item parameter values and verification data may be stored in the at least one target database upon being calculated.

Figure 9:
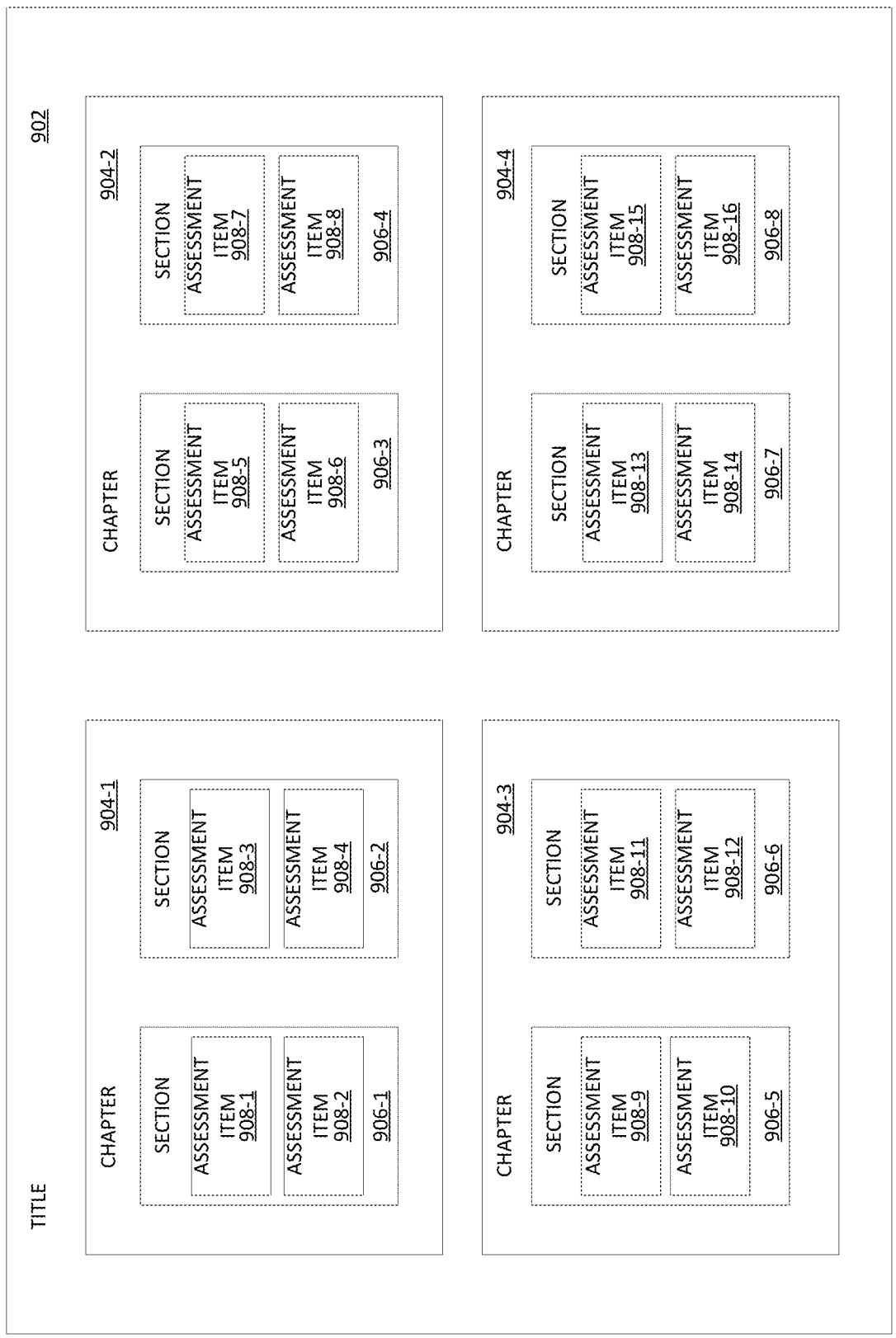
FIG. 9 illustrates an organizational structure of a title that is divided into chapters, which are divided into sections, which are divided into assessment items, which are divided into assessment item parts, in accordance with an embodiment.

FIG. 9 shows the organizational structure of assessment items for a title 902. As used herein, a "title" may refer to an educational course or textbook pertaining to a particular subject, which may be digital (e.g., online). The title 902 may be divided into multiple chapters 904. Each chapter 904 may be divided into multiple sections 906. Each section 906 may include multiple assessment items 908, which may be formative or summative assessment items that evaluate students' (i.e., responders') understanding of content of their corresponding section, chapter, and title. Each assessment item 908 may include one or more assessment item parts. While the title 902 shown here includes four chapters 904, eight sections 906, and sixteen assessment items 908, it should be understood that in other embodiments, the title 902 may include any number of chapters, sections, assessment items, and assessment item parts.

Logical organization of title content may be the basis for division between different sections and between different chapters. For an example in which the title 902 corresponds to a physics course, the chapters may be divided between the subject matter of Mechanics, Properties of Matter, Heat, and Electricity and Magnetism, each having a corresponding chapter of the chapters 904. The chapter 904-1 of the chapters 904 may correspond, for example, to the topic of Electricity and Magnetism, with the section 906-1 including content related to Electrostatics, and the section 906-2 including content related to Electric Fields and Potential (e.g., subjects that fall under the topic of Electricity and Magnetism). Continuing with the example, the section 906-1 may include assessment items 908-1 and 908-2 that provide formative and/or summative assessment of students' understanding of the Electrostatics concepts covered in the section 906-1.

As new content is authored, and new standards for teaching and assessment become available, new editions of educational titles, such as the title 902, may be periodically released by corresponding publishers. However, it may be difficult for the designer or author of a title to accurately assess (i.e., using a sufficiently large sample population) which content of an existing title, including activity content (e.g., assessment item and assessment item part content), should be carried over to a new edition of that title. For a digital title, responses to the assessment item parts of assessment items of the title used or completed by students (e.g., response data) may be collected and stored in one or more computer databases, as described previously. This response data may then be used as a basis for generating key performance indicators (KPIs), sometimes referred to herein as "health scores" or "content health scores," that allow a user to inspect the overall quality of a title at different hierarchical levels (e.g., at the title level, chapter level, section level, assessment item, and assessment item part level). These KPIs may be used to identify underperforming components of a title at any hierarchical level. Such underperforming components may be omitted from new editions of the title and optionally replaced with revised content.

For example, a user (e.g., the author, designer, or administrator responsible for title content) may use title-level KPIs (e.g., title health scores) to rank all titles in a given discipline in order to identify those titles that are underperforming (e.g., having a title health score below a predetermined threshold) and that are therefore in need of revision. The chapters of a selected underperforming title may then be ranked according to chapter-level KPIs (e.g., chapter health score) so that underperforming chapters of the underperforming title may be identified. This process may be repeated at the section level and assessment item level to identify underperforming sections and underperforming assessment items thereof based on section-level KPIs (e.g., section health scores) and assessment-item-level KPIs (e.g., assessment-item health scores), respectively. Once an underperforming assessment item is identified, a set of diagnostic metrics may be shown, allowing issues with the underperforming assessment item to be identified. For example, such issues may include one or more assessment item parts of the underperforming assessment item being too difficult or hints provided for one or more assessment item parts not being sufficiently helpful to decrease the difficulty of the corresponding assessment item parts. These issues may be resolved by rewriting difficult assessment item parts and unhelpful hints, for example. By identifying underperforming content in this way, the cost of authoring new title editions may be reduced by only revising underperforming content of the title when preparing the new title edition. This use of KPIs may also guide revision of titles already "in-market" (i.e., publicly available), allowing for continuous improvement of the content of these titles (e.g., so that content revision and improvement does not need to be delayed until the release of the next edition of the title). These applications of KPIs may help to ensure that existing and new title content is efficacious.

Thus, it may be beneficial to perform a data-based quantitative analysis of the quality of assessment item content of a given title at each hierarchical level of the title.

Figure 10A:
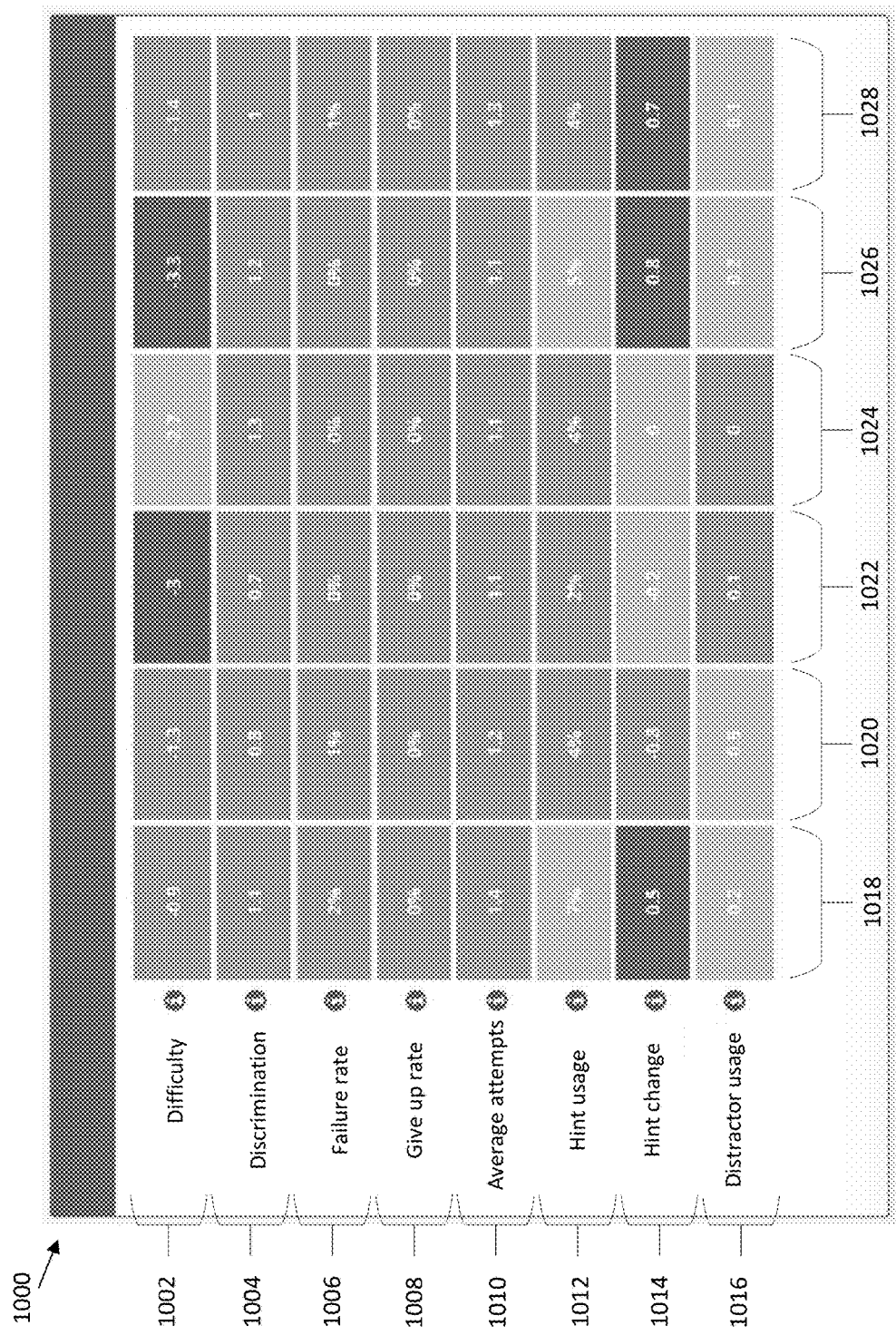
FIG. 10A illustrates a user interface that depicts metric scores for assessment-item-part-level metrics of an assessment item, in accordance with an embodiment.
Figure 10D:
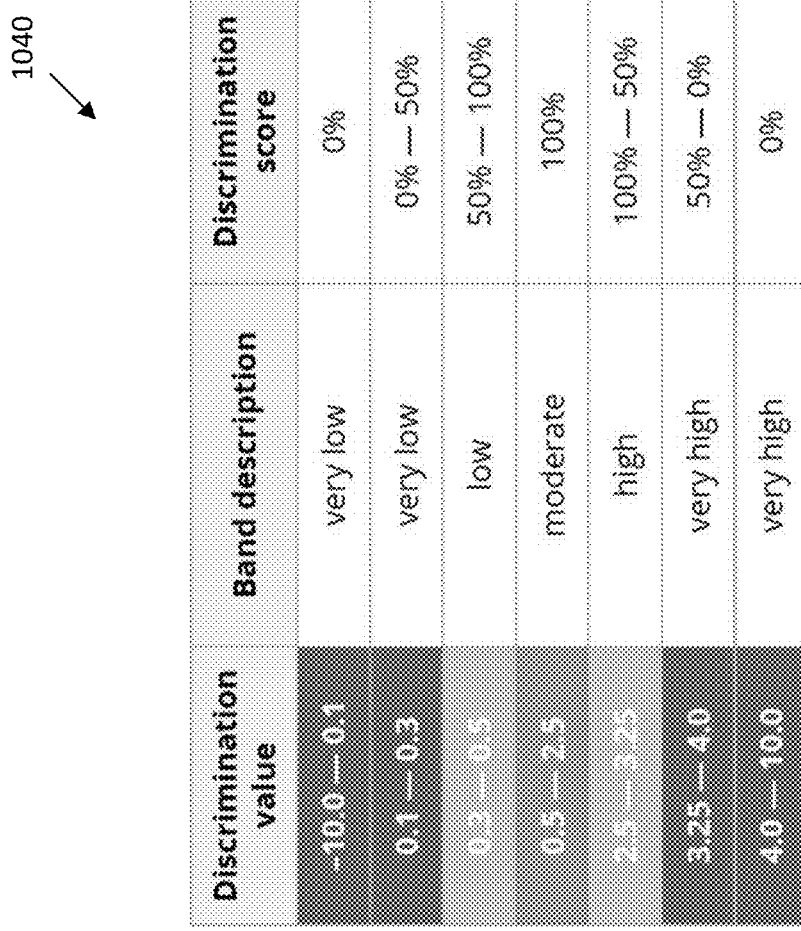
Figure 10E:
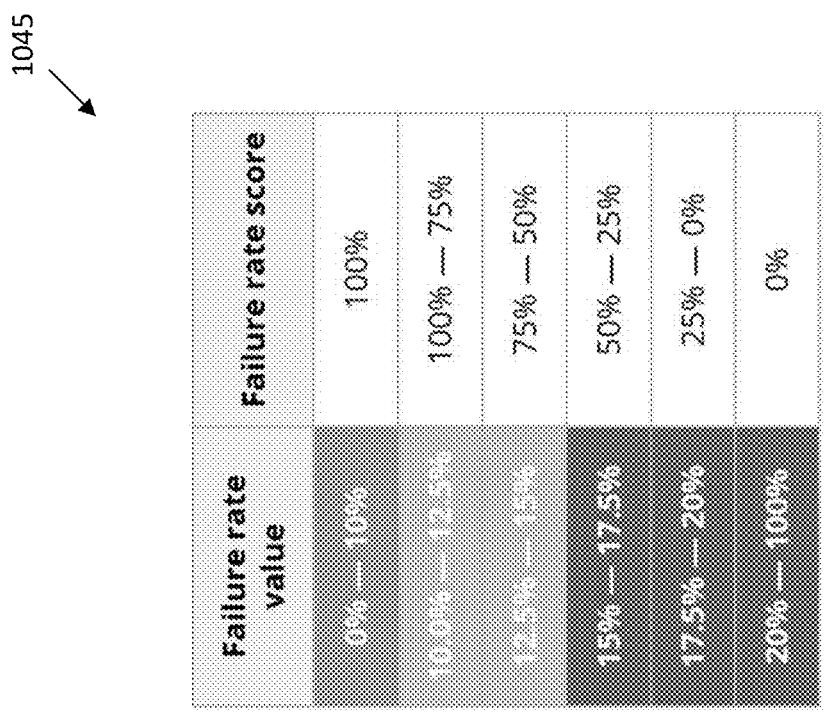
Figure 10F:
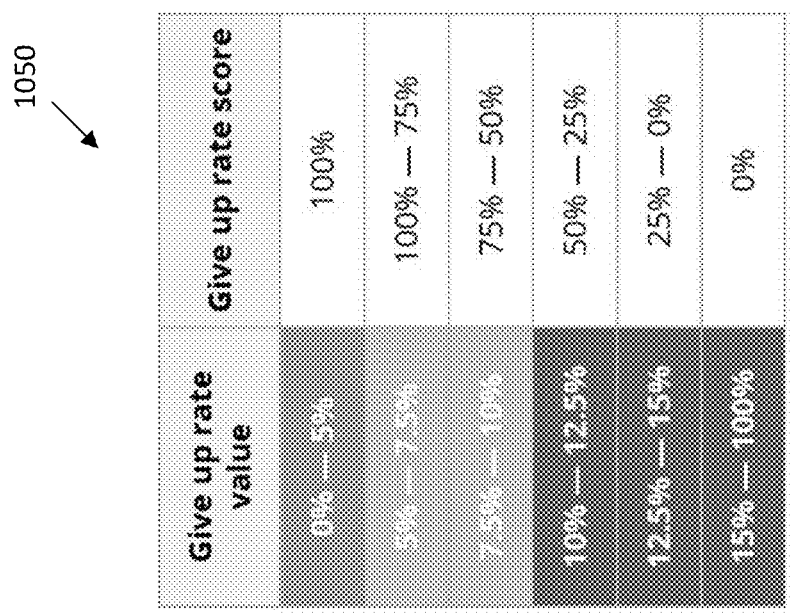
Figure 10G:
Figure 10H:
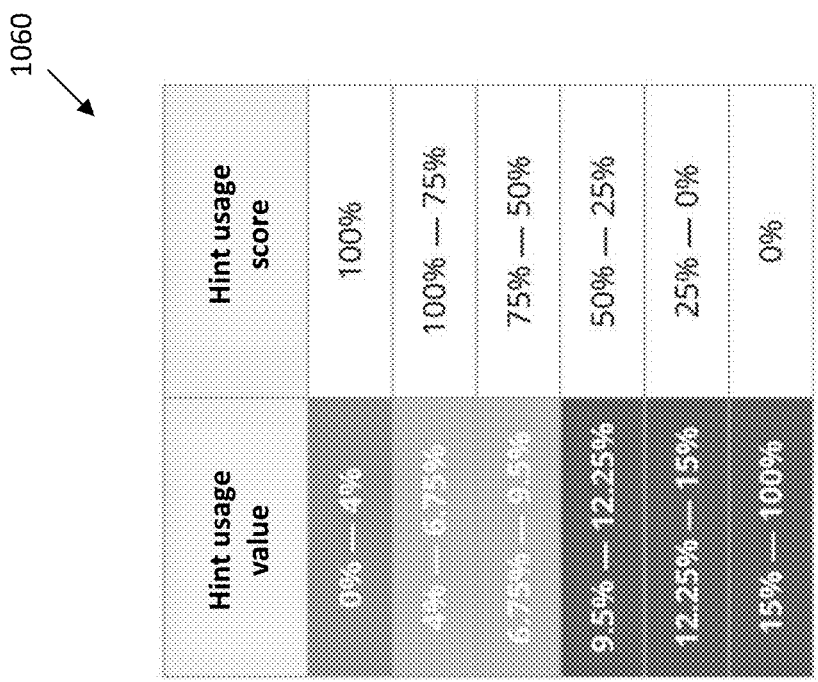
Figure 10I:
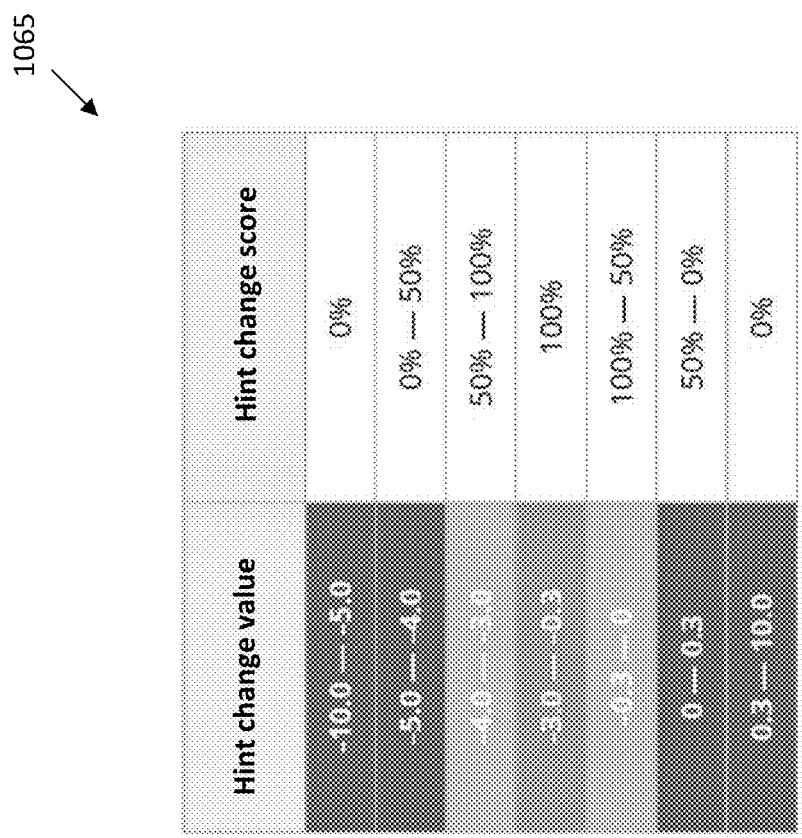
Figure 10J:
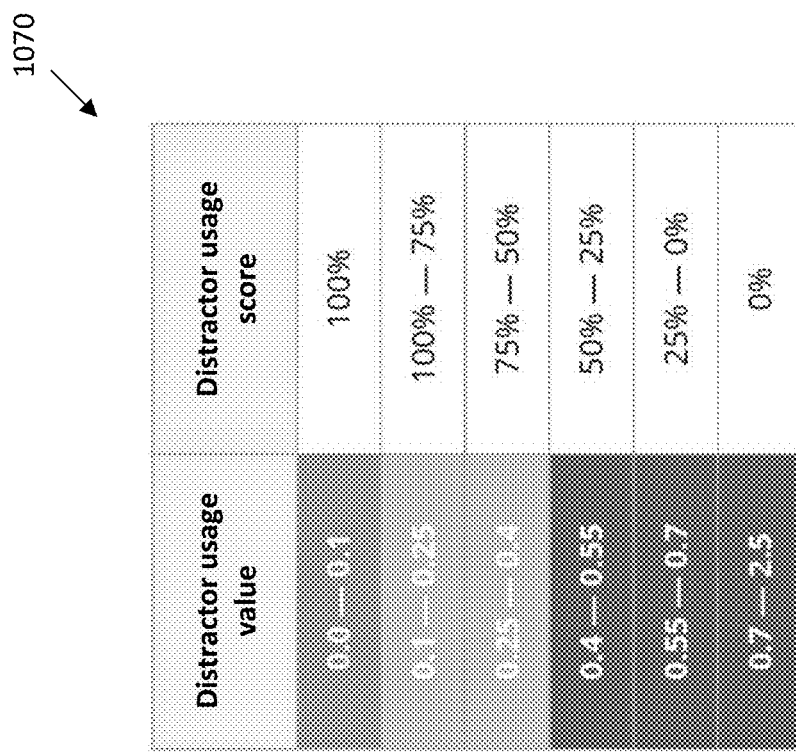

FIG. 10A shows an example user interface 1000 that may be displayed via a display device of a computer system (e.g., computer system 200 of FIG. 2) to show a chart that includes rows of metric values for a variety of assessment-item-part-level metrics including a difficulty metric 1002, a discrimination metric 1004, a failure rate metric 1006, a give up rate metric 1008, an average attempts metric 1010, a hint usage metric 1012, a hint change metric 1014, and a distractor usage metric 1016. Each column of the chart corresponds to a different one of assessment item parts 1018, 1020, 1022, 1024, 1026, and 1028 of an assessment item (e.g., assessment items 908 of FIG. 9). Each of metrics 1002-1016, in addition to having a corresponding metric value for a given assessment item part, may also have a metric score, weight, and reliability value (e.g., each of which may be determined and set by at least one processor of the computer system). Metric data corresponding to the metric value, metric score, metric weight, and metric reliability value for each of the assessment-item-part-level metrics 1002-1016 may be determined for each of the assessment item parts 1018-1028 and may be stored in a remote server (e.g., data store servers 304 of FIG. 3). The metric data may then be used as a basis for calculating an assessment item part health score for each of the assessment item parts 1018-1028, as will be described.

The difficulty metric 1002 may include a difficulty value that is an estimate of the difficulty of a corresponding assessment item part. For example, the difficulty value may be based on an expected the average ability score required for a responder to have a 50% probability of responding to the assessment item part correctly on their first attempt. The difficulty value of an assessment item part may be an estimated value determined using MLE and a 2PL IRT model (e.g., by performing the method 600 of FIG. 6), for example. A difficulty score may be determined based on the difficulty value. An example of how a difficulty score may be determined from a difficulty value for a formative assessment item part (e.g., part of formative assessment items that are generally given as a student progress through a section or chapter) is shown in the illustrative table 1030 of FIG. 10B. It should be understood that the specific metric values, metric scores, and ranges thereof shown in FIGS. 10A-14D are intended to be illustrative and not limiting, and that other applicable values, scores, and ranges may be used for different products or categories of products. An example of how a difficulty score may be determined from a difficulty value for a summative assessment item part (e.g., part of summative assessment items that are generally given at the end of a section or chapter) is shown in the illustrative table 1035 of FIG. 10C. As shown in both table 1030 and table 1035, difficulty value magnitude may be related to difficulty score, such that assessment item parts that are too difficult or too easy are assigned lower scores, while assessment item parts that are of medium difficulty are assigned higher difficulty scores. For example, an assessment item part having a difficulty value of 0 may correspond to medium difficulty, such that an average-skilled responder has a 50% chance of correctly responding to the assessment item part on their first attempt. The difficulty score may be used as a basis for determining an assessment item part health score for the corresponding assessment item part.

The discrimination metric 1004 may include a discrimination value that is an estimate of how well an assessment item part can discriminate between responders of different ability levels. For example, the discrimination value of a given assessment item part may be quantified as the local rate of change of a corresponding item characteristic curve (e.g., shown in chart 800 of FIG. 8) at a midpoint of the item characteristic curve (e.g., corresponding to a 50% probability of a responder providing a correct response to the assessment item part on their first attempt). A lower discrimination value may indicate that the assessment item part is less likely to discriminate between learners of different ability levels compared to a desired (e.g., predetermined rate). The discrimination value of an assessment item part may be an estimated value determined using MLE and a modified 2PL IRT model (e.g., by performing the method of FIG. 6) or an unmodified 2PL IRT model, for example. An example of how a discrimination score may be determined from a discrimination value for an assessment item part is shown in the illustrative table 1040 of FIG. 10D. As shown, negative discrimination values (e.g., indicative of an assessment item part for which lower-ability responders are more likely to respond correctly than higher-ability responders) are determined to have a discrimination score of 0%, as they are do not discriminate between responders well based on ability. Discrimination values that are too high (e.g., greater than 3.25) are also determined to have lower discrimination scores in the present example, as they discriminate too narrowly based on ability (e.g., such that substantially all responders above a given ability score are expected to respond correctly, while those below the given ability score are expected to respond incorrectly). The discrimination score may be used as a basis for determining an assessment item part health score for the corresponding assessment item part.

The failure rate metric 1006 may include a failure rate value that is a percentage of all responders to the corresponding assessment item part who ultimately fail to provide a correct answer to the assessment item part, regardless of the number attempts made by the individual responder or whether the individual responder exhausted all allowed attempts. An example of how a failure rate score may be determined from a failure rate value for an assessment item part is shown in the illustrative table 1045 of FIG. 10E. As shown, the determined failure rate score may be inversely related to failure rate values from 0% to 20%, and may be 0% for all failure rate values greater than 20%, such that assessment item parts for which many students fail may receive lower scores. The failure rate score may be used as a basis for determining an assessment item part health score for the corresponding assessment item part.

The give up rate metric 1008 may include a give up rate value that is a percentage of all responders to the corresponding assessment item part who ultimately fail to provide a correct answer to the assessment item part without exhausting all allowed attempts at responding to the assessment item part. An example of how a give up rate score may be determined from a give up rate value for an assessment item part is shown in the illustrative table 1050 of FIG. 10F. As shown, the determined give up rate score may be inversely related to give up rate values from 0% to 15%, and may be 0% for all give up rate values greater than 15%, such that assessment item parts for which many students fail without utilizing all possible attempts at responding to those assessment item parts may receive lower scores. The give up rate score may be used as a basis for determining an assessment item part health score for the corresponding assessment item part.

The average attempts metric 1010 may include an average attempts value that represents the average number of attempts needed to be made by individual responders before they are able to provide a correct response to the corresponding assessment item part. An example of how an average attempts score may be determined from an average attempts value for an assessment item part is shown in the illustrative table 1055 of FIG. 10G. As shown, for both formative and summative assessment items, the average attempts value is inversely related to the average attempts score, such that the average number of attempts required before a responder correctly responds to the assessment item part, when lower, corresponds to a higher score and, when higher, corresponds to a lower score. Additionally, as shown, how average attempts scores are determined may differ based on whether a given assessment item part is formative or summative, and whether the given assessment item part has multiple inputs (e.g., multiple choice problems), or single input (e.g., problems that accept a string input). For example, the average attempts value ranges for assessment item parts having a single input may have somewhat higher upper thresholds than the corresponding average attempts value ranges for assessment item parts having multiple inputs, as single input assessment item parts tend to be more complex, therefore requiring comparatively more attempts on average. The average attempts score may be used as a basis for determining an assessment item part health score for the corresponding assessment item part.

The hint usage metric 1012 may include a hint usage value that is a percentage of learners who request hints on their first attempt when responding to a given assessment item part. An example of how a hint usage score may be determined from a hint usage value for an assessment item part is shown in the illustrative table 1060 of FIG. 10H. As shown, the determined hint usage score may be inversely related to the hint usage values from 0% to 15%, and may be 0% for all hint usage values greater than 15% such that assessment item parts for which hints are relied upon too heavily may receive lower scores. The hint usage score may be used as a basis for determining an assessment item part health score for the corresponding assessment item part.

The hint change metric 1014 may include a hint change value that is an estimate of the effect that requesting a hint prior to a responder's first attempt at responding to a corresponding assessment item part has on the difficulty (e.g., the difficulty value) of the assessment item part. The hint change value may be measured as an expected shift in assessment item part difficulty value, with negative hint change values corresponding to a decrease in difficulty value, and positive hint change values corresponding to an increase in difficulty value. For example, the hint change value may be estimated using MLE based on a modified 2PL IRT model (e.g., according to the method 600 of FIG. 6). An example of how a hint change score may be determined from a hint change value for an assessment item part is shown in the illustrative table 1065 of FIG. 10I. As shown, the hint change score may be inversely related to the magnitude of the hint change values, such that assessment item parts having hints that have too little or too great of an effect on the difficulty of the corresponding assessment item part receive lower scores. The hint change score may be used as a basis for determining an assessment item part health score for the corresponding assessment item part.

The distractor usage metric 1016 may include a distractor usage value that corresponds to the difference in the usage of distractors on responders' their first attempts at responding to a corresponding assessment item part. As used here, a "distractor" refers to an incorrect response choice provided to someone attempting to respond to a multiple-choice assessment item part, where the incorrect response choice is sufficiently plausible to distract the responder from selecting the correct response. Examples of distractors may include common errors or misconceptions, statements that are true but that do not answer the question posed by the assessment item part, and content that is incorrectly phrased. An example of how a distractor usage score may be determined from a distractor usage value for an assessment item part is shown in the illustrative table 1070 of FIG. 10J. As shown, the determined distractor usage score may be inversely related to the distractor usage values from 0 to 0.7, and may be 0% for all distractor usage values greater than 0.7 such that assessment item parts for which distractors are selected frequently may be determined to have lower scores (e.g., it may not be beneficial to include a distractor that is too effective at distracting from the correct response). The distractor usage score may be used as a basis for determining an assessment item part health score for the corresponding assessment item part.

Each of the assessment-item-part-level metrics 1002-1016 may be assigned (e.g., by at least one processor of a computer system) a predetermined metric weight (sometimes referred to as a "weight" or "weight value") based on the importance of that metric. For example, difficulty metrics 1002 may be assigned a weight of 1 for summative assessment item parts and a weight of 0.8 for formative assessment item parts, discrimination metrics 1004 may be assigned a weight of 1, hint change metrics 1014 may be assigned a weight of 1 for assessment item parts for which at least one responder used a hint and a weight of 0 otherwise, hint usage metrics 1012 may be assigned a weight of 1 for assessment item parts for which hints are available to be used and for which the hint usage value is positive and may be assigned a weight of 0 otherwise, the average attempts metric 1010 may be assigned a weight of 1 for formative assessment item parts and a weight of 0.8 for summative assessment item parts, the failure rate metric 1006 may be assigned a weight of 1, the give up rate metric 1008 may be assigned a weight of 1, and the distractor usage metric 1016 may be assigned a weight of 0.7. Assessment item parts with essay inputs may have a weight of 0. As will be described the weights assigned to different metrics across different hierarchical content levels may vary from metric-to-metric, based upon the level of impact each metric is desired to have on the content health scores that it is used as a basis for calculating.

A reliability value may be determined for each of the assessment-item-part-level metrics 1002-1116 for each of the assessment item parts 1018-1028. Each reliability value may be a value between 0 and 1, with 0 indicating that the corresponding metric score is completely unreliable (e.g., because not enough responders interacted with the content), and a 1 indicating that the corresponding metric score is very reliable (e.g., the associated metric score was calculated with a high level of accuracy).

For example, the same reliability value may be provided for the difficulty metric 1002 and discrimination metric 1004 of a given assessment item part. Discrimination and difficulty metric reliability may be determined (e.g., by at least one processor of a computer system) using the following equation:

$$R_{D_{1,2}} = S_{IRT\_size} \cdot (1 - |CFT - \bar{y}|) \quad \text{(Eq. 3)}$$

where $R_{D_{1,2}}$ represents the reliability value for both the difficulty metric 1002 and the discrimination metric 1004 an assessment item part, $S_{IRT\_size}$ represents an IRT sample size score that is based on the sample size of the sample population of responders used to calculate the difficulty and discrimination values for the assessment item part, CFT represents a percentage of responders that correctly responded to the assessment item part on their first attempt, and $\bar{y}$ represents the average probability of a correct first response to the assessment item part (e.g., estimated via the application of the modified 2PL IRT model described previously). It should be understood that Eq. 3 is intended to be illustrative and not limiting. For example, $S_{IRT\_size}$ may be set equal to 1 if more than 500 responders submitted responses to the assessment item part, 0 if less than 100 responders submitted responses to the assessment item part, and may otherwise be calculated using the following equation:

$$S_{IRT\_size} = \left(\frac{\text{sample size}}{400} - 0.25\right)^3 \quad \text{(Eq. 4)}$$

where sample size represents the number of responders that submitted responses to the assessment item part. It should be understood that Eq. 4 is intended to be illustrative and not limiting.

The reliability of the hint change metric 1014 may be determined (e.g., by at least one processor of a computer system) using the following equation:

$$R_{hint\_change} = S_{hint\_size} \cdot (1 - |CFT - \bar{y}|) \quad \text{(Eq. 5)}$$

where $R_{hint\_change}$ represents the reliability value of the hint change metric 1014, and $S_{hint\_size}$ represents a hint usage sample size score that is based on the number of responders who used a hint when responding to the assessment item part. It should be understood that Eq. 5 is intended to be illustrative and not limiting. For example, $S_{hint\_size}$ may be set equal to 1 if more than 100 responders used a hint when responding to the assessment item part, may be set equal to 0 if less than 20 responders used a hint when responding to the assessment item part, and may otherwise be calculated using the following equation:

$$S_{hint\_size} = \left(\frac{\text{hint sample size}}{80} - 0.25\right)^3 \quad \text{(Eq. 6)}$$

where hint sample size represents the number of responders that used a hint when responding to the assessment item part. It should be understood that Eq. 6 is intended to be illustrative and not limiting.

For the remaining assessment-item-part-level metrics 1006, 1008, 1010, 1012, and 1016, corresponding reliability values may be determined based simply on the number of responders who submitted a response to the assessment item part. For example, the reliability value of any of metrics 1006, 1008, 1010, 1012, and 1016 for an assessment item part may be set equal to 1 if more than 100 responders submitted a response to the assessment item part, may be set equal to 0 if less than 20 responders submitted a response to the assessment item part, and may otherwise be determined (e.g., by at least one processor of a computer system) using the following equation:

$$R_m = \left(\frac{\text{sample size}}{80} - 0.25\right)^3 \quad \text{(Eq. 7)}$$

where $R_m$ represents the reliability value of the metric, and sample size represents the number of responders that submitted responses to the assessment item part. It should be understood that Eq. 7 is intended to be illustrative and not limiting.

Based on the assessment-item-part-level metrics 1002-1016 (and their associated scores, weights, and reliability values), an assessment item part health score may be determined for each of the assessment item parts 1018-1028.

Health scores at all hierarchical levels, including assessment item part health scores, assessment item health scores, section health scores, chapter health scores, and title health scores, may be calculated (e.g., by at least one processor of a computer system) using the following equation:

$$H = \frac{\sum_{m \in M_c} (s_{c,m} \cdot w_{c,m} \cdot r_{c,m})}{\sum_{m \in M_c} (w_{c,m} \cdot r_{c,m})} \quad \text{(Eq. 8)}$$

where H represents the health score, m represents a metric of a set of metrics M for a given content c (e.g., an assessment item part, an assessment item, a section, a chapter, or a title), s represents the score of the metric m, w represents the weight of the metric m, and r represents the reliability of the metric m. As shown the health score H for the content c is calculated as the sum of the product of the score s, weight w, and reliability r of each metric m of the set of metrics M for the content c divided by the sum of the product of the weight w and reliability r of each metric m of the set of metrics M for the content c. It should be understood that Eq. 8 is intended to be illustrative and not limiting.

It should be understood that all health scores, metric values, scores, weights, and reliability values may updated periodically (e.g., as new response data becomes available as new responders submit responses to assessment item parts of a title) and may be stored in one or more databases of one or more servers (e.g., the data store server 304 of FIG. 3) subsequent to their determination by a processor of a corresponding computer system (e.g., computer system 200 of FIG. 2). User interfaces, such as those shown in FIGS. 10A, 11A, 12A, 13A, and 14A when generated for display at an electronic display of a client device (e.g., client devices 106 of FIG. 1) may be populated with corresponding content health scores and, optionally, corresponding metric values retrieved from these one or more databases.

Figure 11A:
FIG. 11A illustrates a user interface that depicts an assessment-item health score and assessment-item-level metrics for a digital assessment, in accordance with an embodiment.
Figure 11C:
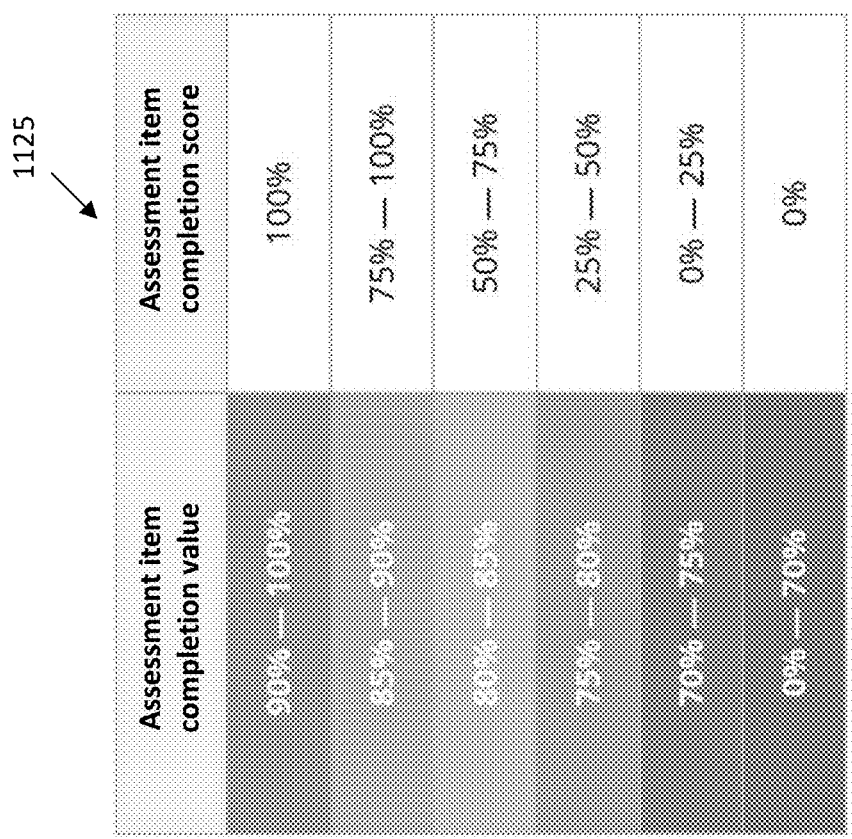
Figure 11D:
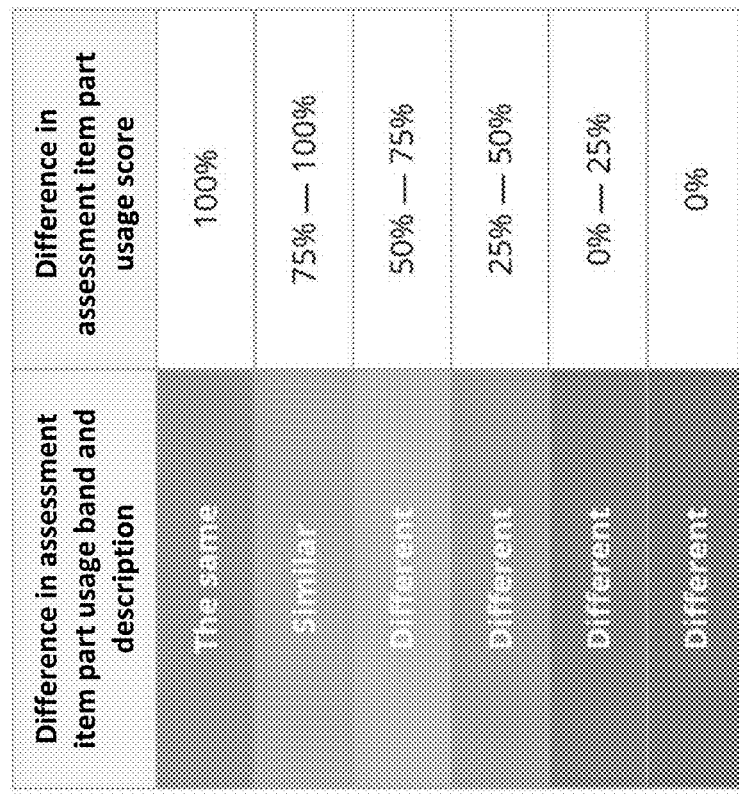
Figure 11E:
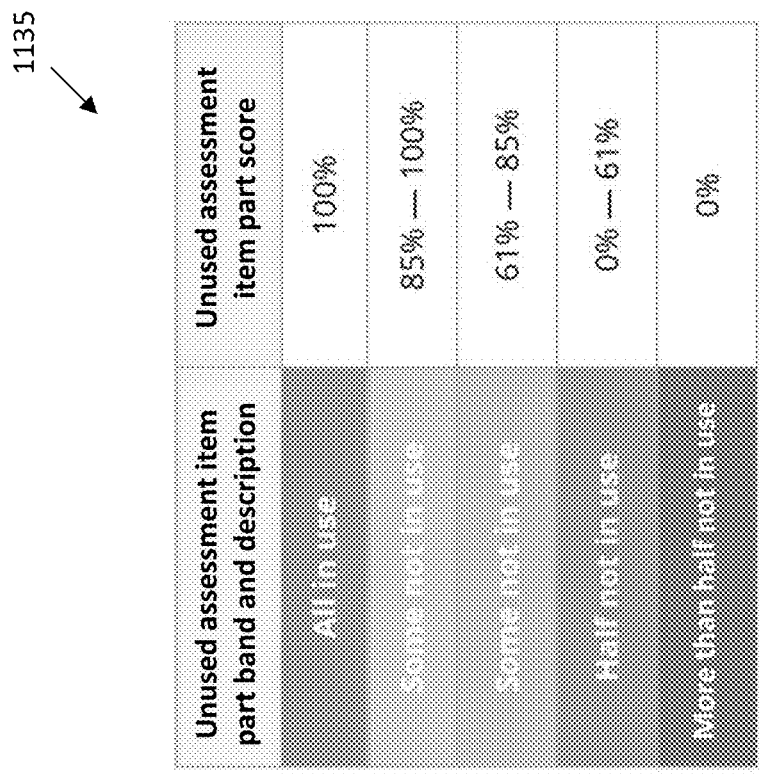
Figure 11G:
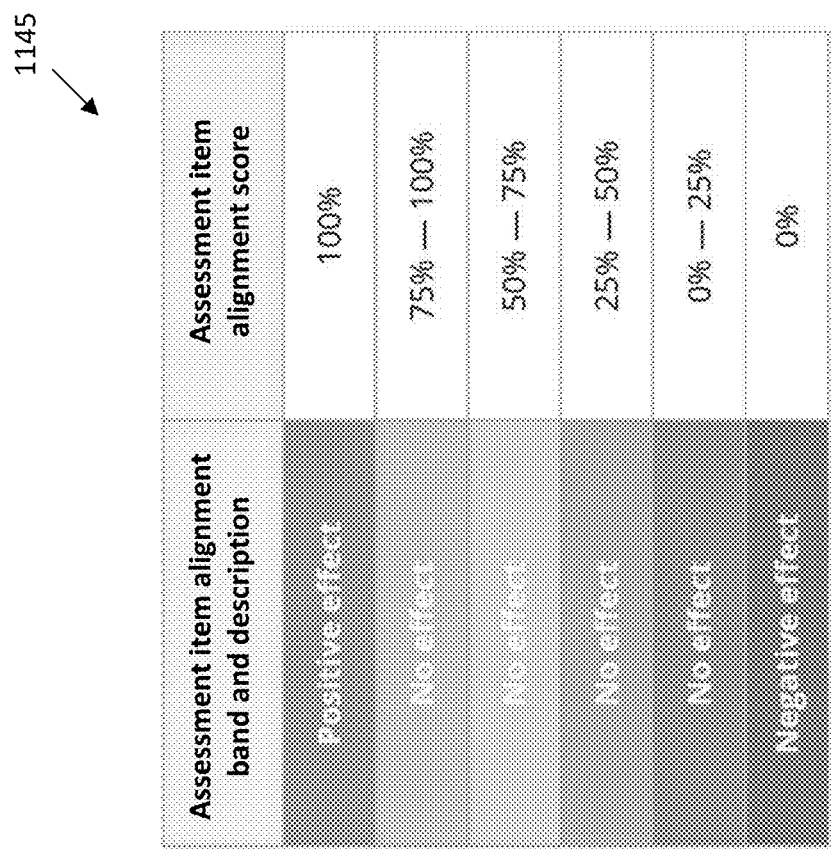
Figure 11H:
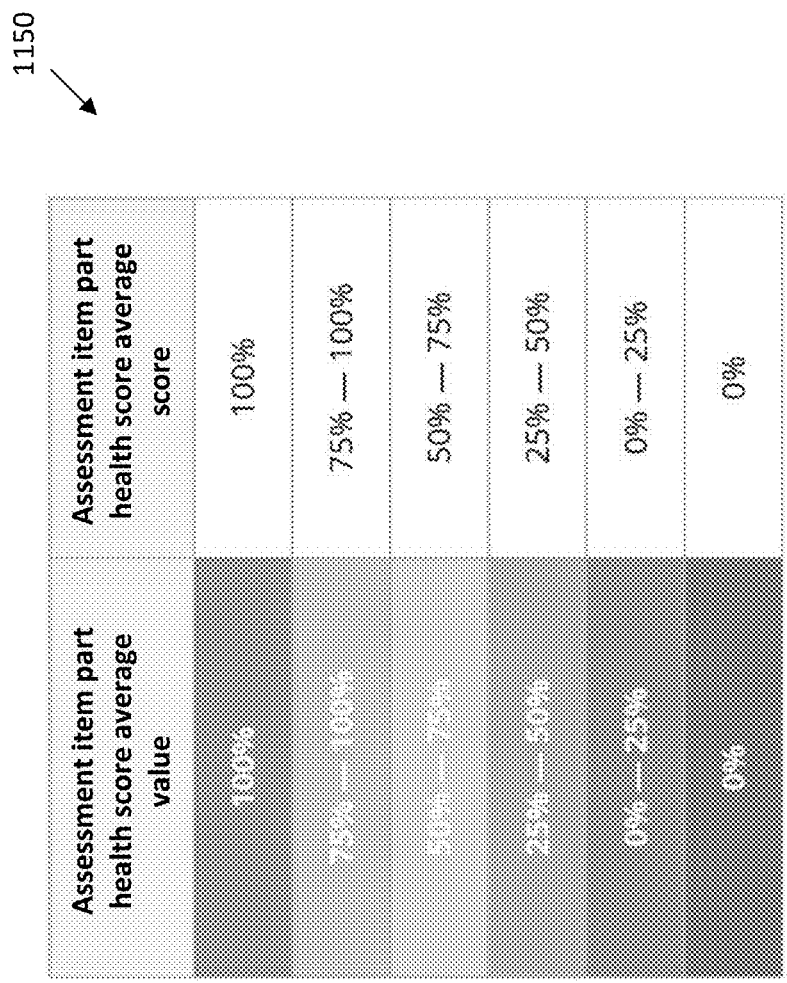

FIG. 11A shows an example user interface 1100 that may be displayed via a display device of a computer system (e.g., computer system 200 of FIG. 2) that includes an assessment item health score 1102 and assessment-item-level metrics 1104-1116. The assessment item health score 1102 may correspond to an assessment item (e.g., assessment items 908 of FIG. 9). The assessment-item-level metrics include an assessment item usage metric 1104, an assessment item completion rate 1106, a difference in assessment item part usage metric 1108, an unused assessment item parts metric 1110, an assessment item part health score difference metric 1112, an assessment item alignment metric 1114, and an assessment item part health score average metric 1116. Metric data corresponding to the value, score, weight, and reliability value for each of the assessment-item-level metrics 1104-1116 may be stored in a remote server (e.g., data store servers 304 of FIG. 3), and may be used as a basis for calculating the assessment item health score 1102 for the assessment item, as will be described.

The assessment item usage metric 1104 may include an assessment item usage value that represents a percentage of the number of responders who used the assessment item (e.g., submitted at least one response to any assessment item part of the assessment item) to the total number of responders who used assessment items in a section of which the assessment item is a part. An example of how an assessment item usage score may be determined from an assessment item usage value for an assessment item is shown in the illustrative table 1120 of FIG. 11B. As shown, the determined assessment item usage score may be set to 0% for assessment item usage values from 0% to 0.5%, may increase from 0% to 100% as assessment item usage values increase from 0.5% to 2%, and may be set to 100% for assessment item usage values that exceed 2%. In this way assessment items that are underutilized may receive lower scores. The assessment item usage score may be used as a basis for determining the assessment item health score 1102 for the corresponding assessment item. The weight of the assessment item usage metric 1104 may be 0.5. The reliability of the assessment item usage metric 1104 for a given assessment item may be 1 if the average number of responders who used the given assessment item is greater than 100, 0 if lower than 20, and may be calculated according to equation, and may be calculated according to Eq. 9, below, otherwise.

$$R_{aium} = \left(\frac{\text{sample size}}{80} - 0.25\right)^2 \quad \text{(Eq. 9)}$$

Where $R_{aium}$ is the reliability value for the assessment item usage metric 1104, and where the sample size corresponds to the average number of responders who used the given assessment item. It should be understood that Eq. 9 is intended to be illustrative and not limiting.

The assessment item completion rate metric 1106 may include an assessment item completion value that represents a percentage of responders that completed the assessment item (e.g., that submitted correct responses to each assessment item part of the assessment item within an allowed number of attempts) to the total number of responders for the assessment item. An example of how an assessment item completion score may be determined from an assessment item completion value for an assessment item is shown in the illustrative table 1125 of FIG. 11C. As shown, the determined assessment item completion score may be set to 0% for assessment item usage values from 0% to 70%, may increase from 0% to 100% as assessment item usage values increase from 70% to 90%, and may be set to 100% for assessment item usage values that exceed 90%. In this way assessment items having a relatively large number of responders that have not completed the assessment item may receive lower scores. The assessment item completion score may be used as a basis for determining the assessment item health score 1102 for the corresponding assessment item. The assessment item completion rate metric 1106 may have a weight of 0.5. The reliability score of the assessment item completion rate metric 1106 may be determined in the same way as that of the assessment item usage metric 1104.

The difference in assessment item part usage metric 1108 may represent a difference in assessment item part usage value that represents a difference between a number of responders who used (e.g., submitted at least one response to) the most often used assessment item part of the assessment item and a number of responders who used the least often used part of the assessment item, the difference being divided by the number of responders who used the most often used assessment item part of the assessment item. An example of how a difference in assessment item part usage score may be determined from a difference in assessment item part usage value for an assessment item is shown in the illustrative table 1130 of FIG. 11D. As shown, as the number of students that respond to the most often used assessment item part becomes more similar to that of students that respond to the least often used assessment item part, the corresponding score increases. In this way, assessment items that include underutilized assessment item parts may be identified as having lower difference in assessment item part usage scores. The difference in assessment item part usage score may be used as a basis for determining the assessment item health score 1102 for the corresponding assessment item. The weight of the assessment item part usage metric 1108 may be 0 if a given assessment item includes only one assessment item part, and may be 0.3 otherwise. The reliability value of the assessment item part usage metric 1108 for a given assessment item may be 1 if the maximum number of responders who used the given assessment item is greater than 100, 0 if less than 20, and determined according to Eq. 10, below, otherwise.

$$R_{aipum} = \left(\frac{\text{sample size}}{80} - 0.25\right)^2 \quad \text{(Eq. 10)}$$

Where $R_{aipum}$ is the reliability value for the assessment item part usage metric 1108, and sample size corresponds to the maximum number of responders who used the given assessment item. It should be understood that Eq. 10 is intended to be illustrative and not limiting.

The unused assessment item parts metric 1110 may include an unused assessment item parts value that represents a percentage of the number of assessment item parts of an assessment item that are used by at least one responder to the total number of assessment item parts included in the assessment item. An example of how an unused assessment item parts score may be determined from a unused assessment item parts value for an assessment item is shown in the illustrative table 1135 of FIG. 11E. As shown, as the number of unused assessment item parts decreases, the corresponding score increases. In this way, assessment items that include higher percentages of unused assessment item parts may be identified as having lower unused assessment item parts scores. The unused assessment item parts score may be used as a basis for determining the assessment item health score 1202 for the corresponding assessment item. The weight of the unused assessment item parts metric 1110 may be 0 if there is only one assessment item part in a given assessment item, and the lower of 0.3 or six one-hundredths of the number of assessment item parts of the given assessment item, otherwise.

The assessment item part health score difference metric 1112 may include an assessment item part health score difference value that represents a difference between a weighted arithmetic average of the assessment item part health scores and a weighted harmonic average of the assessment item part health scores for all of the assessment item parts included in the assessment item. An example of how an assessment item part health score difference score may be determined from an assessment item part health score difference value for an assessment item is shown in the illustrative table 1140 of FIG. 11F. As shown, as the average difference between assessment item part health scores of an assessment item increases, the corresponding score decreases. In this way, assessment items that include assessment item parts having substantially inconsistent (e.g., different) health scores may be identified as having lower assessment item part health score difference scores. The assessment item part health score difference score may be used as a basis for determining the assessment item health score 1102 for the corresponding assessment item. The assessment item part health score difference metric 1112 may have a weight of 0 if only one assessment item part of a given assessment item is used, and a weight of 0.8, otherwise. The reliability value of the assessment item part health score difference metric 1112 for a given assessment item may be an average (e.g., mean) of the reliability values of the assessment item part health scores of all assessment item parts in the given assessment item.

The assessment item alignment metric 1114 may include an assessment item alignment value that represents an estimated effect that a responder completing a formative assessment item (e.g., submitting correct responses to each of the assessment item parts of the formative assessment item within an allowed number of attempts) has on that responder's performance on a corresponding summative assessment item. An example of how an assessment item alignment score may be determined from an assessment item alignment value for an assessment item is shown in the illustrative table 1145 of FIG. 11G. As shown, as the assessment item alignment increases, the corresponding score increases. The assessment item alignment score may be used as a basis for determining the assessment item health score 1102 for the corresponding assessment item. The weight of the assessment item alignment metric 1114 may be 0 if an assessment item alignment isn't available for a given assessment item, and 0.8 otherwise. The reliability value of the assessment item alignment metric 1114 may be 0 if the number of responders who used a given assessment item is lower than 20, and 1 otherwise.

The assessment item part health score average metric 1116 may include an assessment item part health score average value that represents an average of the health scores of all assessment item parts included in the corresponding assessment item. An example of how an assessment item part health score average score may be determined from an assessment item part health score average value for an assessment item is shown in the illustrative table 1150 of FIG. 11H. As shown, the assessment item part health score average score may be set equal to the assessment item part health score average value. The assessment item health score average score may be used as a basis for determining the assessment item health score 1102 for the corresponding assessment item. The weight of the assessment item part health score average metric 1116 for a given section may be 1. The reliability value of the assessment item part health score average metric 1116 for a given section may be an average (e.g., mean) of the reliability values of the assessment item part health scores of all assessment item parts in the given assessment item.

The assessment item health score 1102 may be determined based on the score, weight, and reliability value of each of the assessment-item-level metrics 1104-1116.

Figure 12A:
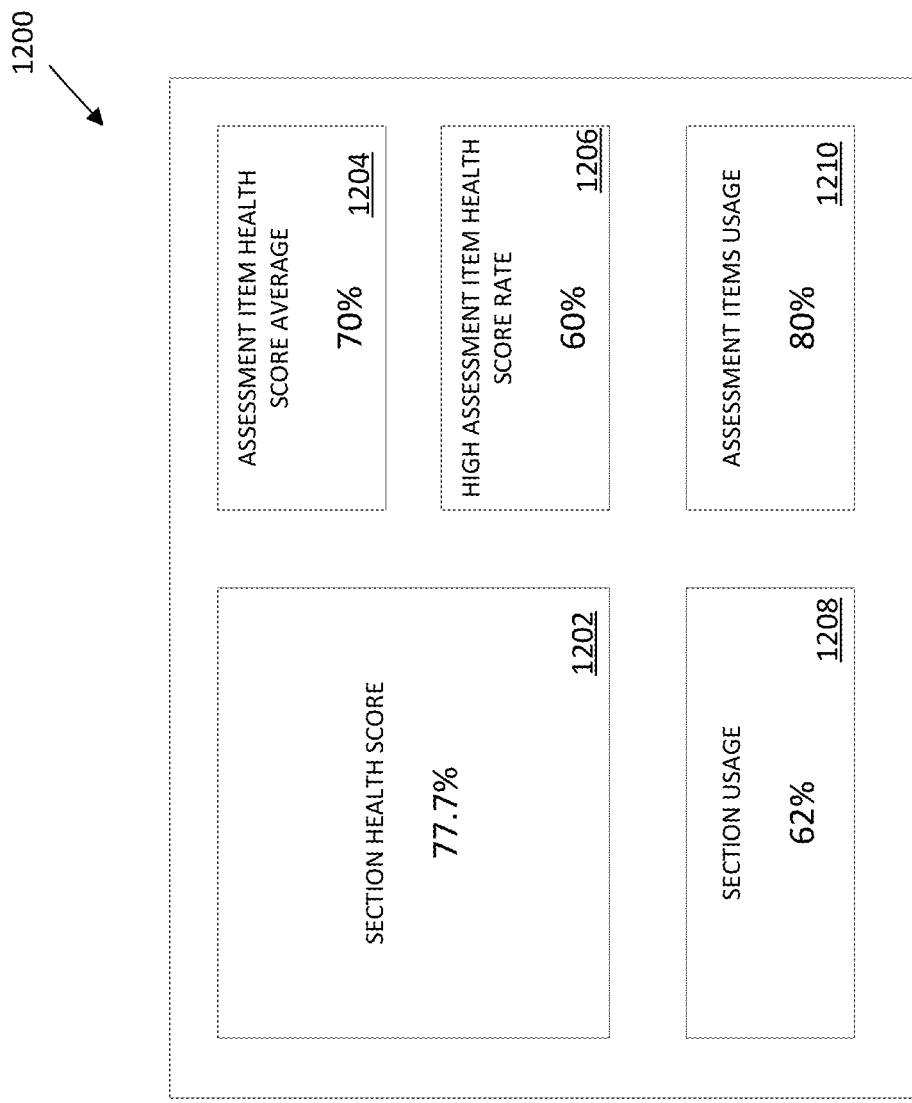
FIG. 12A illustrates a user interface that depicts a section health score and section-level metrics for a section containing one or more assessment items, in accordance with an embodiment.
Figure 12B:
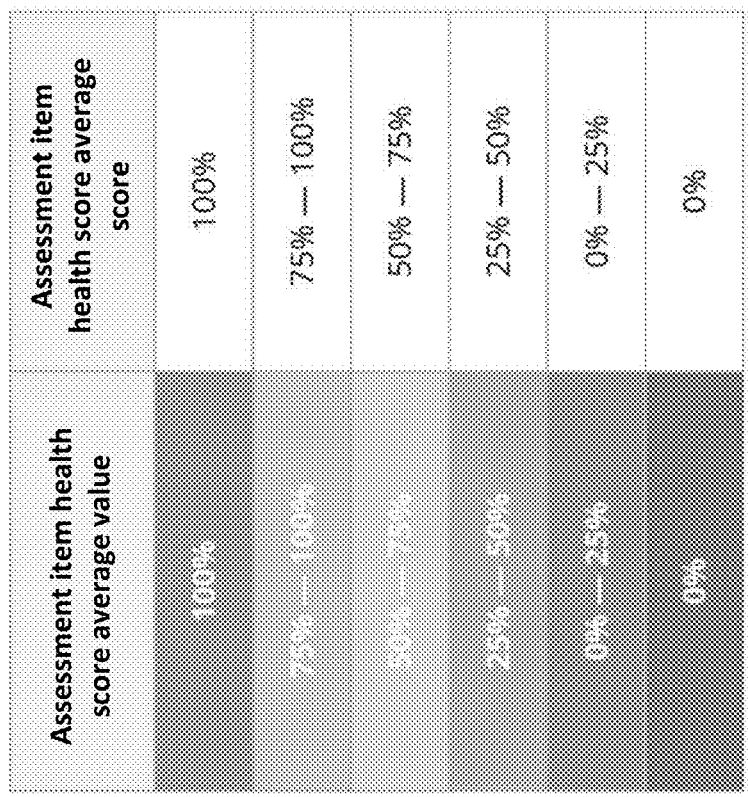
FIGS. 12B-12E illustrate tables depicting relationships between section-level metric values and section-level metric scores that may be used in determining section health scores, in accordance with an embodiment.
Figure 12C:
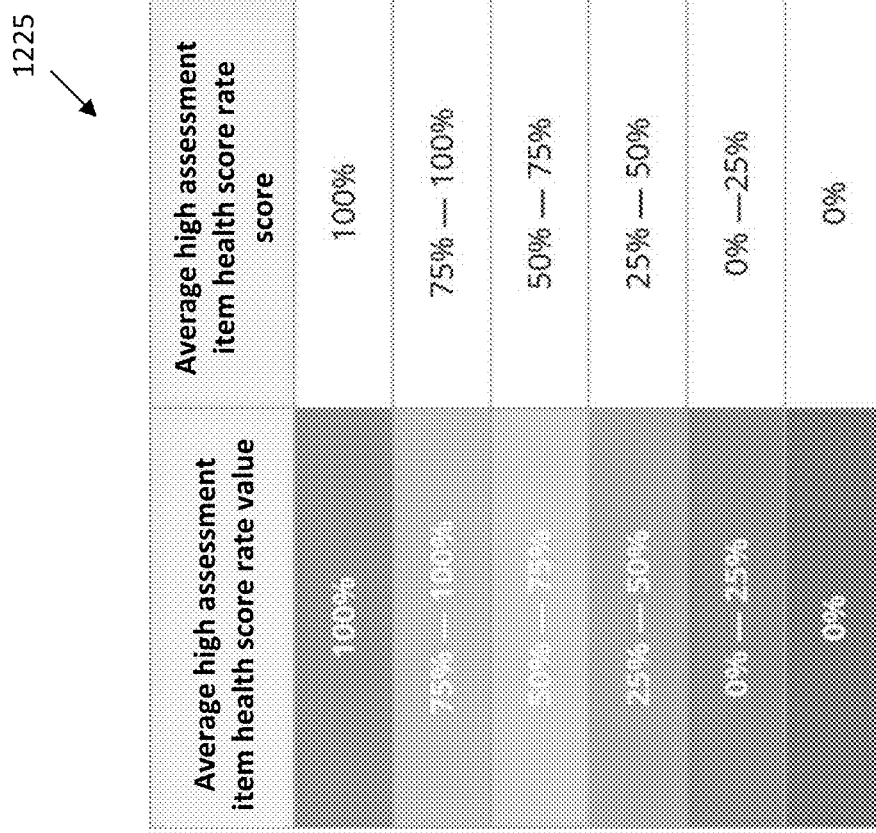
Figure 12D:
Figure 12E:
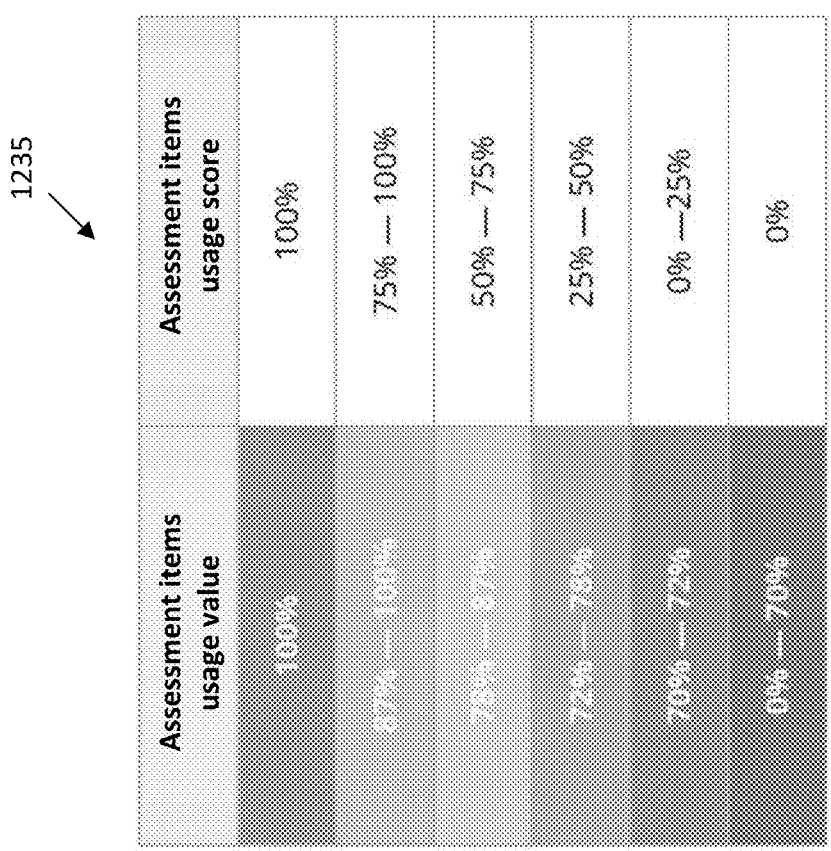

FIG. 12A shows an example user interface 1200 that may be displayed via a display device of a computer system (e.g., computer system 200 of FIG. 2) that includes a section health score 1202 and section-level metrics 1204-1210. The section health score 1202 may correspond to a section (e.g., sections 906 of FIG. 9) containing one or more digital assessment items (e.g., assessment items 908 of FIG. 9). The section-level metrics may include an assessment item health score average metric 1204, an average high assessment item health score rate metric 1206, a section usage metric 1208, and an assessment items usage metric 1210. Metric data corresponding to the value, score, weight, and reliability value for each of the section-level metrics 1204-1210 may be stored in a remote server (e.g., data store servers 304 of FIG. 3), and may be used as a basis for calculating the section health score 1302 of the section, as will be described.

The assessment item health score average metric 1204 may include an assessment item health score average value that represents an average of the health scores of all assessment items included in the corresponding section. An example of how an assessment item health score average score may be determined from an assessment item health score average value for a section is shown in the illustrative table 1220 of FIG. 12B. As shown, the assessment item health score average score may be set equal to the assessment item health score average value. The assessment item health score average score may be used as a basis for determining the section health score 1202 for the corresponding section. The weight of the assessment item health score average metric 1204 for a given section may be 1. The reliability value of the assessment item health score average metric 1204 for a given section may be an average (e.g., mean) of the reliability values of the assessment item health scores of all assessment items in the given section.

The average high assessment item health score rate metric 1206 may include an average high assessment item health score rate value that represents a weighted average of mapped assessment item health scores a given section, weighted by the respective reliability values of those assessment item health scores. For example, if the assessment item has a health score lower than 0.6, it is mapped to 0, if the assessment item has a health score higher than 0.8, it is mapped to 1, and if the assessment item has a health score between 0.6 and 0.8, it is mapped to a score between 0 and 1. An example of how an average high assessment item health score rate score may be determined from an average high assessment item health score rate value for a section is shown in the illustrative table 1225 of FIG. 12C. As shown, the average high assessment item health score rate score may be set equal to the average high assessment item health score rate value. The average high assessment item health score rate score may be used as a basis for determining the section health score 1202 for the corresponding section. The weight for the average high assessment item health score rate metric 1206 of a given section may be 1. The reliability value of the average high assessment item health score rate metric 1206 for a given section may be an average (e.g., mean) of the reliability values of the assessment item health scores of all assessment items in the given section.

The section usage metric 1208 may include a section usage value that represents a percentage of the number of responders that used assessment items (e.g., responded to at least one assessment item part of at least one of the assessment items) of a corresponding section to the number of responders who used assessment items of a chapter of which the corresponding section is a part. An example of how a section usage score may be determined from a section usage value for a section is shown in the illustrative table 1230 of FIG. 12D. As shown, the section usage score may be set to 0% for section usage values between 0% and 10%, may increase from 0% to 100% as section usage values increase from 10% to 50%, and may be set to 100% for section usage values over 50%. The section usage score may be used as a basis for determining the section health score 1202 for the corresponding section. The weight of the section usage metric 1208 for a given section may be 0 it is the only section in its chapter, and 0.3 otherwise. The reliability value of the section usage metric 1208 for any section may be 1.

The assessment items usage metric 1210 may include an assessment items usage value that represents a percentage of the number of assessment items used (e.g., assessment items for which at least one responder has submitted a response to at least one assessment item part thereof) in the corresponding section to the total number of assessment items available in that section. An example of how an assessment items usage score may be determined from an assessment items usage value for a section is shown in the illustrative table 1235 of FIG. 12E. As shown, the assessment items usage score may be set to 0% for assessment items usage values between 0% and 70%, may increase from 0% to 100% as assessment items usage values increase from 70% to 100%. The assessment items usage score may be used as a basis for determining the section health score 1202 for the corresponding section. The weight of the assessment items usage metric 1210 may be 0.3. The reliability value of the assessment items usage metric 1210 may be 1.

The section health score 1202 may be determined based on the score, weight, and reliability value of each of the section-level metrics 1204-1210.

Figure 13A:
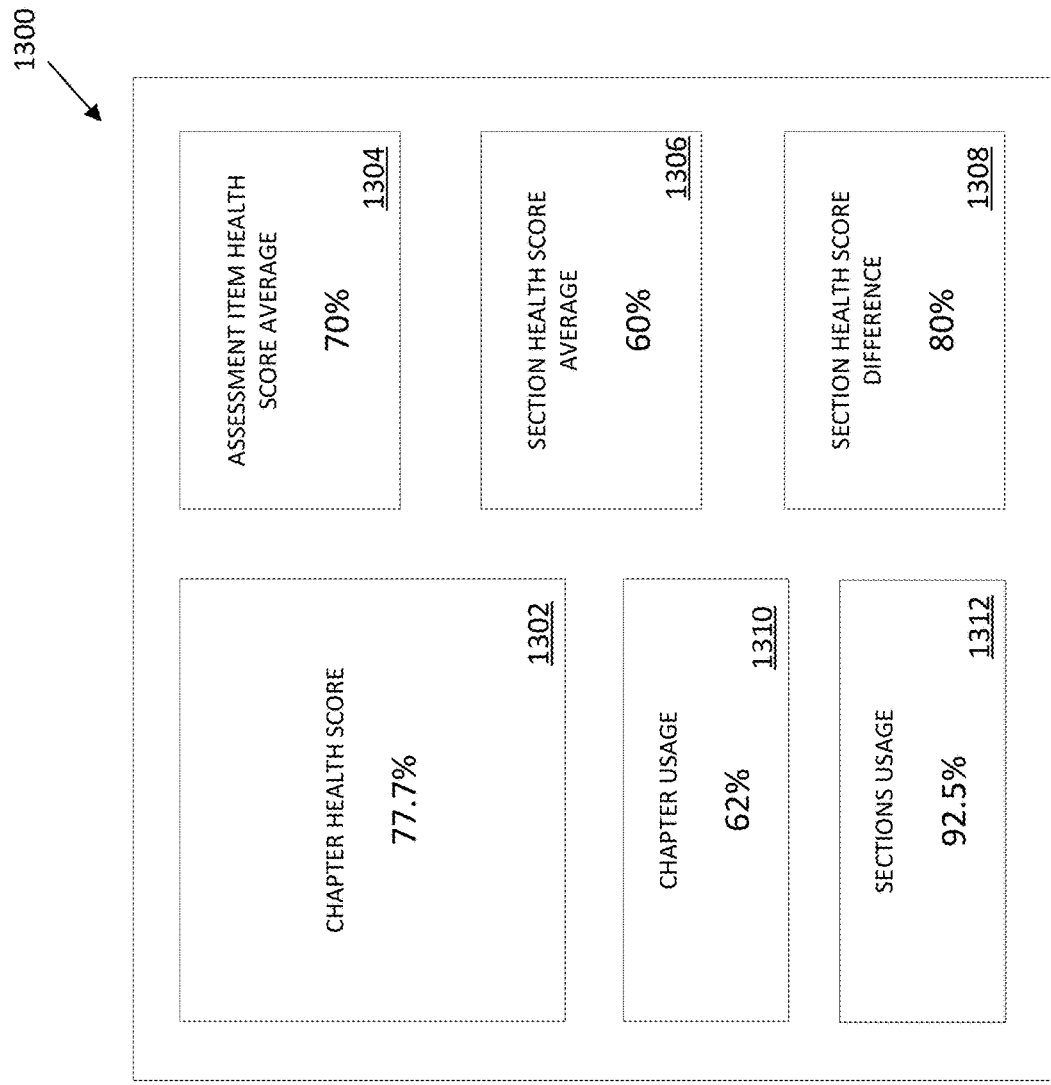
FIG. 13A illustrates a user interface that depicts a chapter health score and chapter-level metrics for a chapter containing one or more sections containing one or more assessment items, in accordance with an embodiment.
Figure 13B:
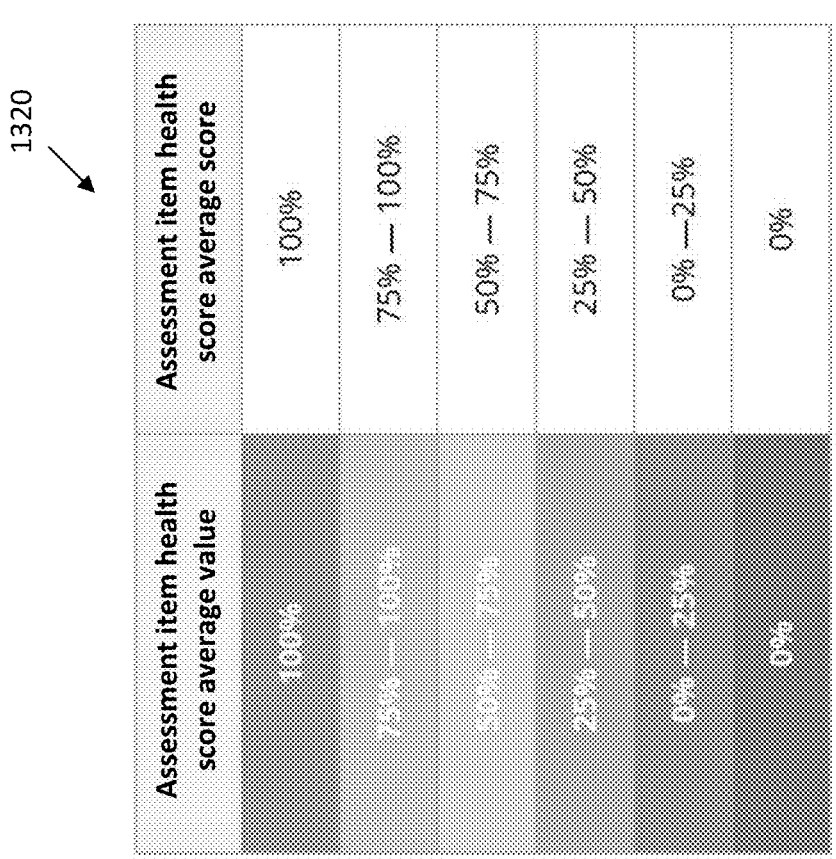
FIG. 13B-13F illustrate tables depicting relationships between chapter-level metric values and chapter-level metric scores that may be used in determining chapter health scores, in accordance with an embodiment.
Figure 13C:
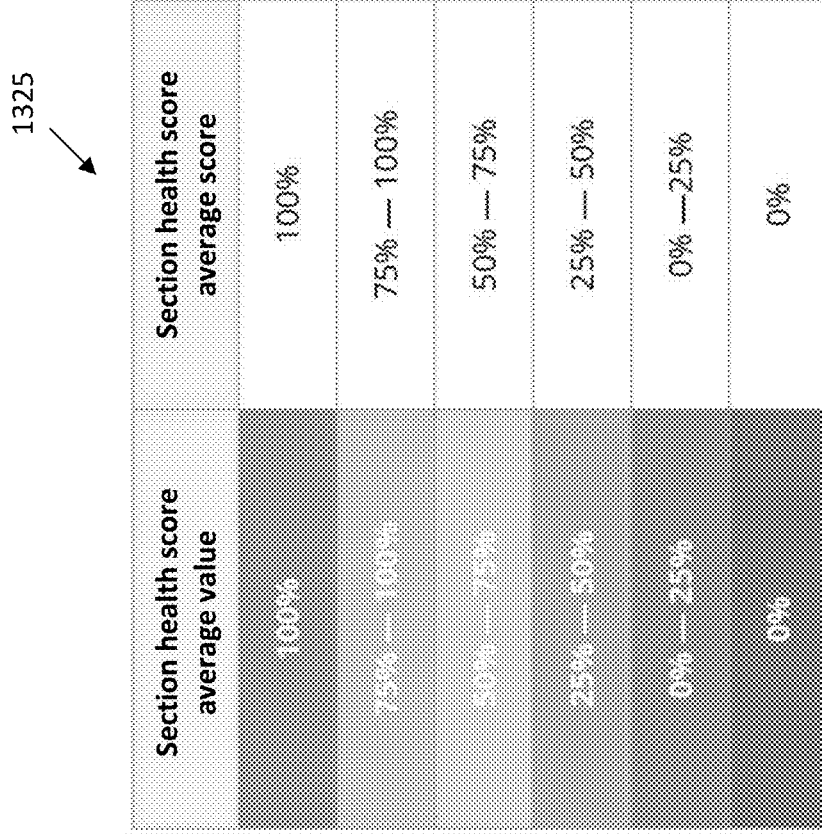
Figure 13D:
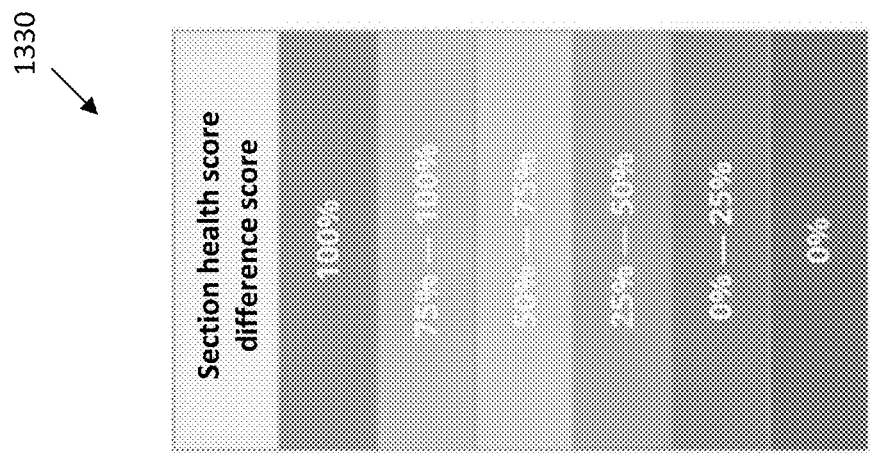
Figure 13E:
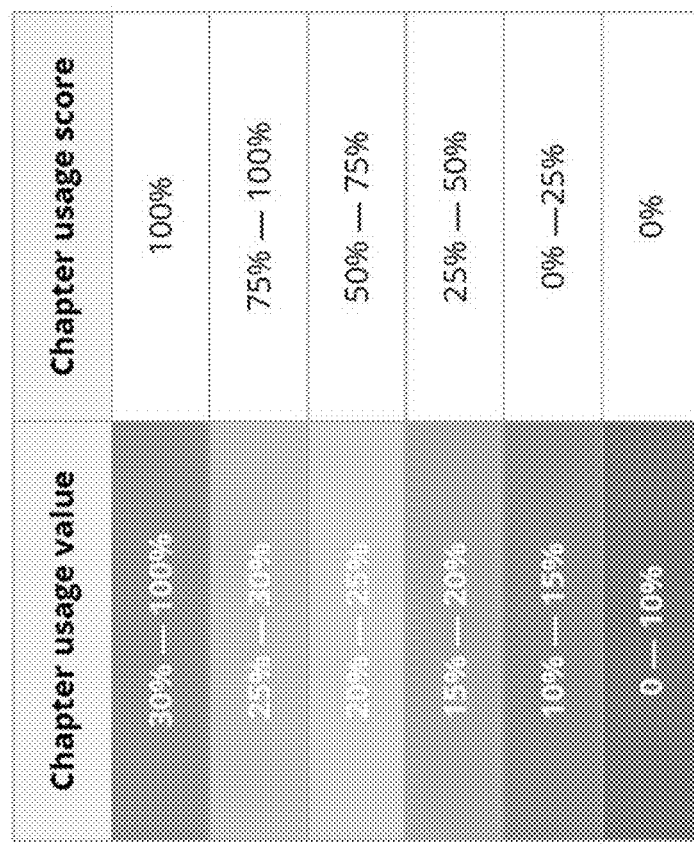
Figure 13F:
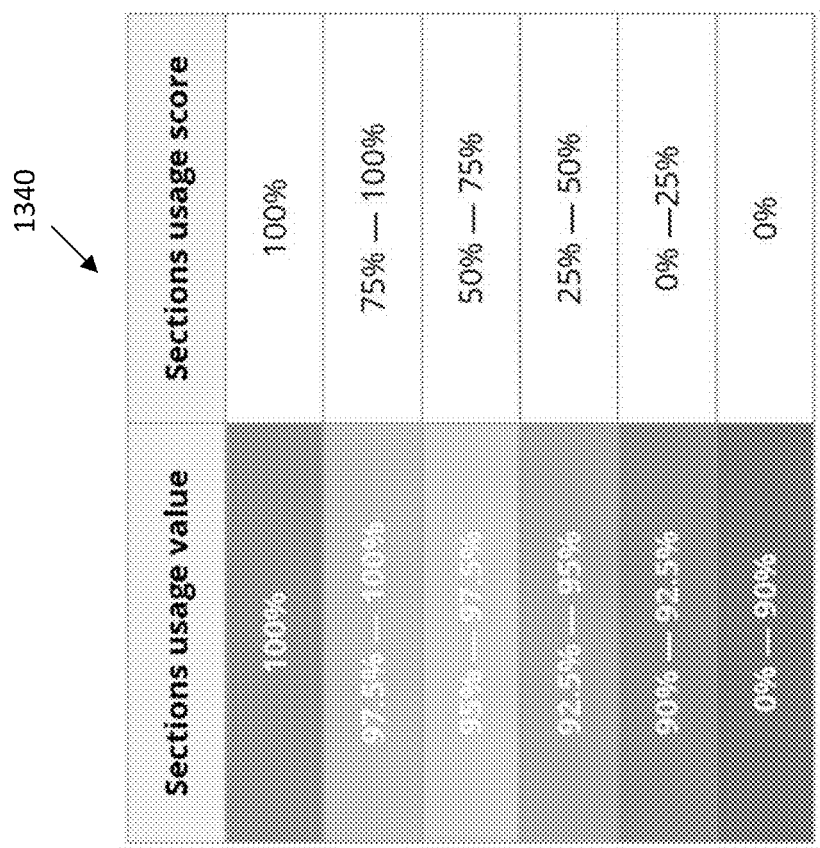

FIG. 13A shows an example user interface 1300 that may be displayed via a display device of a computer system (e.g., computer system 200 of FIG. 2) that includes a chapter health score 1302 and chapter-level metrics 1304-1312. The chapter health score 1302 may correspond to a chapter (e.g., chapters 904 of FIG. 9) containing one or more sections (e.g., sections 906 of FIG. 9), each containing one or more digital assessment items (e.g., assessment items 908 of FIG. 9). The chapter-level metrics include an assessment item health score average metric 1304, a section health score average metric 1306, a section health score difference metric 1308, a chapter usage metric 1310, and a sections usage metric 1312. Metric data corresponding to the value, score, weight, and reliability value for each of the chapter-level metrics 1304-1312 may be stored in a remote server (e.g., data store servers 304 of FIG. 3), and may be used as a basis for calculating the chapter health score 1302 of the chapter, as will be described.

The assessment item health score average metric 1304 may include an assessment item health score average value that represents an average of the health scores of all assessment items in all sections included in the corresponding chapter. An example of how an assessment item health score average score may be determined from an assessment item health score average value for a chapter is shown in the illustrative table 1320 of FIG. 13B. As shown, the assessment item health score average score may be set equal to the assessment item health score average value. The assessment item health score average score may be used as a basis for determining the chapter health score 1302 for the corresponding chapter. The weight of the assessment item health score average metric 1304 for a given chapter may be 1. The reliability value for the assessment item health score average metric 1304 for a given chapter may be an average (e.g., mean) of the reliability values of the assessment item health scores of all assessment items in the given chapter.

The section health score average metric 1306 may include a section health score average value that represents an average of the health scores of all sections included in the corresponding chapter. An example of how a section health score average score may be determined from a section health score average value for a chapter is shown in the illustrative table 1325 of FIG. 13C. As shown, the section health score average score may be set equal to the section health score average value. The section health score average score may be used as a basis for determining the chapter health score 1302 for the corresponding chapter. The weight of the section health score average metric 1306 for a given chapter may be 1. The reliability value for the section health score average metric 1306 of a given chapter may be an average (e.g., mean) of the reliability values of the section health scores of all sections in the given chapter.

The section health score difference metric 1308 may include a section health score difference value that represents a difference between a weighted arithmetic average of section health scores and a weighted harmonic average of section health scores for all of the sections included in the chapter. An example of how a section health score difference score may be determined from a section health score difference value for a chapter is shown in the illustrative table 1330 of FIG. 13D. The section health score difference score may be used as a basis for determining the chapter health score 1302 for the corresponding chapter. The weight of the section health score difference metric 1308 of a given chapter may be 0 if there is only one section in the given chapter, and 0.8 otherwise. The reliability value for the section health score difference metric 1308 for a given chapter may be an average (e.g., mean) of the reliability values of the section health scores of all sections in the given chapter.

The chapter usage metric 1310 may include a chapter usage value that represents a percentage of the number of responders that used assessment items (e.g., responded to at least one assessment item part of at least one of the assessment items) of at least one section of the corresponding chapter to the number of responders who used assessment items of a title of which the corresponding chapter is a part. An example of how a chapter usage score may be determined from a chapter usage value for a section is shown in the illustrative table 1335 of FIG. 13E. As shown, the chapter usage score may be set to 0% for chapter usage values between 0% and 10%, may increase from 0% to 100% as chapter usage values increase from 10% to 30%, and may be set to 100% for chapter usage values over 30%. The chapter usage score may be used as a basis for determining the chapter health score 1302 for the corresponding chapter. The weight of the chapter usage metric 1310 for a given chapter may be 0.2. The reliability value for the chapter usage metric 1310 for a given chapter may be 1.

The sections usage metric 1312 may include a sections usage value that represents a percentage of the number of sections used (e.g., sections for which at least one responder has submitted a response to at least one assessment item part of at least one assessment item thereof) in the corresponding chapter to the total number of sections available in that chapter. An example of how a sections usage score may be determined from a sections usage value for a section is shown in the illustrative table 1340 of FIG. 13F. As shown, the sections usage score may be set to 0% for sections usage values between 0% and 90%, and may increase from 0% to 100% as sections usage values increase from 90% to 100%. The sections usage score may be used as a basis for determining the chapter health score 1302 for the corresponding chapter. The weight for the section usage metric 1312 of a given chapter may be 0 if all sections of the given chapter were used, and may be 0.4 if at least one of the sections of the given chapter were not used. The reliability value for the section usage metric 1312 of a given chapter may be 1.

The chapter health score metric 1302 may be determined based on the score, weight, and reliability value of each of the chapter-level metrics 1304-1312.

Figure 14A:
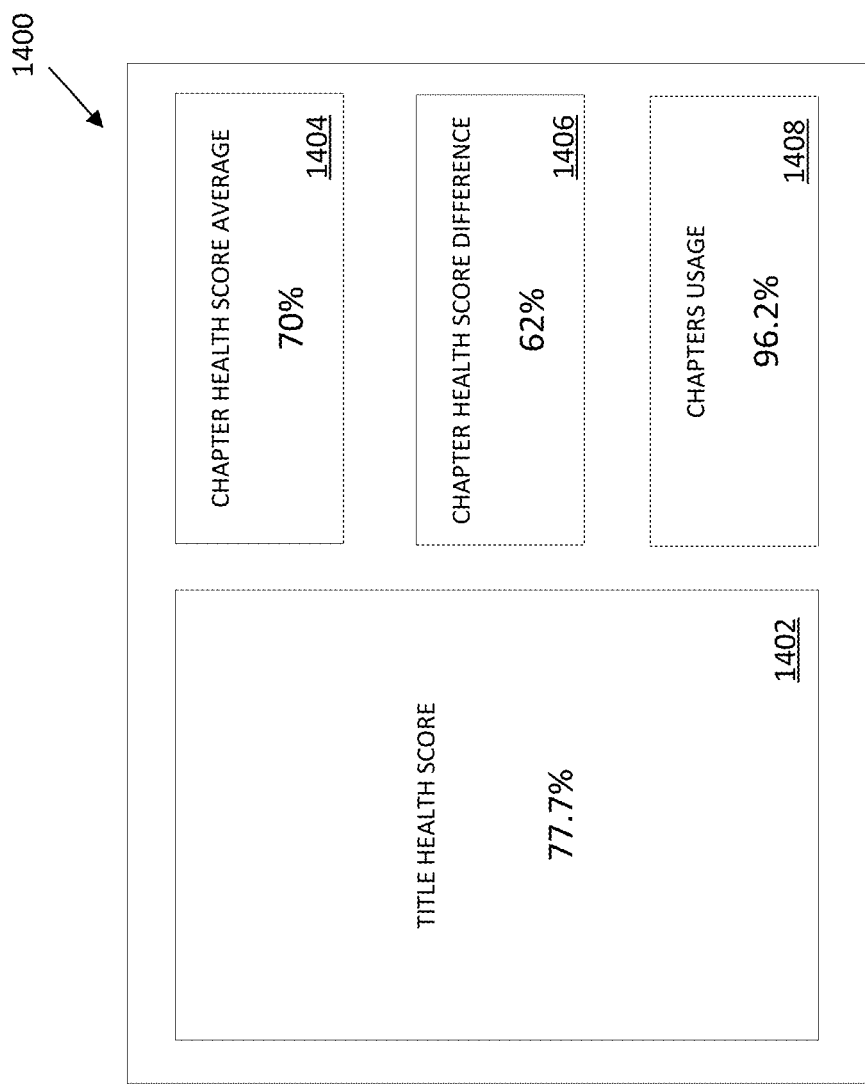
FIG. 14A illustrates a user interface that depicts a title health score and title-level metrics for a title containing one or more chapters containing one or more sections containing one or more assessment items, in accordance with an embodiment.
Figure 14B:
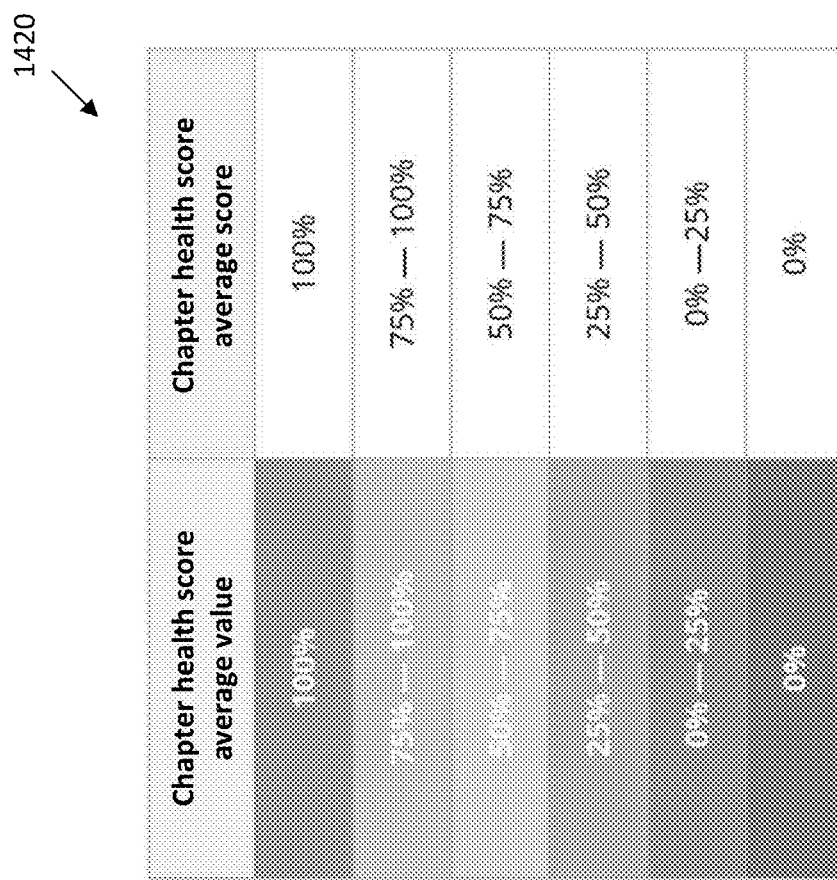
FIGS. 14B-14D illustrate tables depicting relationships between title-level metric values and title-level metric scores that may be used in determining title health scores, in accordance with an embodiment.
Figure 14C:
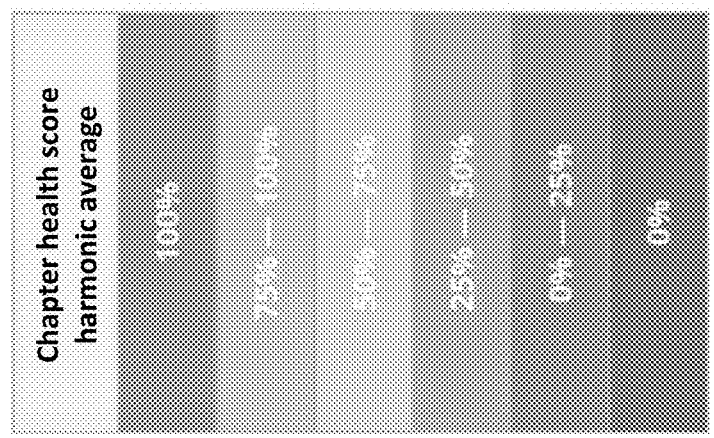
Figure 14D:
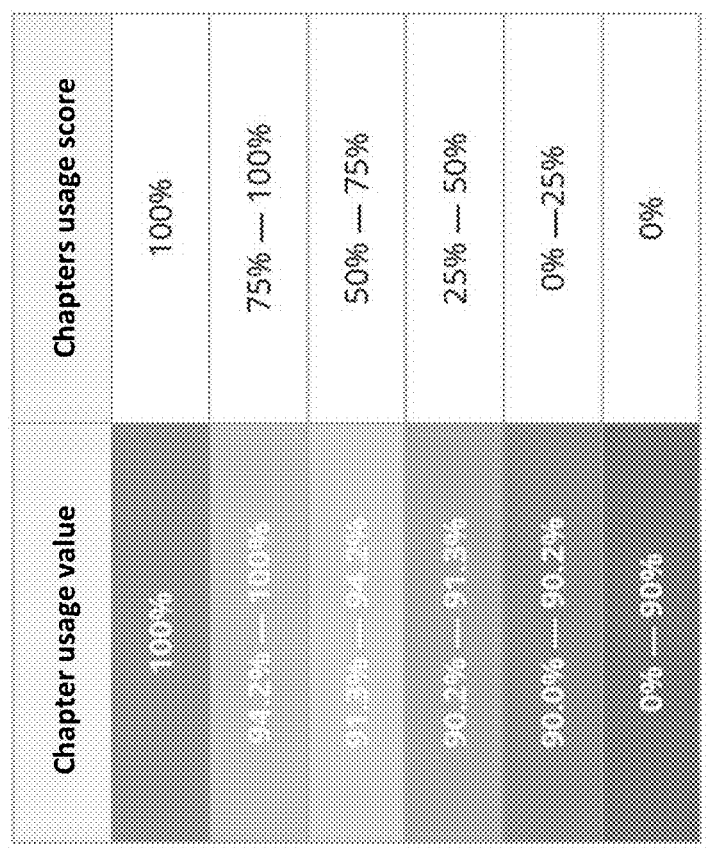

FIG. 14A shows an example user interface 1400 that may be displayed via a display device of a computer system (e.g., computer system 200 of FIG. 2) that includes a title health score 1402 and title-level metrics 1504-1506. The title health score 1402 may correspond to a title (e.g., title 902 of FIG. 9) containing one or more chapters (e.g., chapters 904 of FIG. 9), each containing one or more sections (e.g., sections 906 of FIG. 9), each containing one or more digital assessment items (e.g., assessment items 908 of FIG. 9). The title-level metrics include a chapter health score average metric 1404, a chapter health score difference metric 1406, and a chapters usage metric 1408. Metric data corresponding to the value, score, weight, and reliability value for each of the title-level metrics 1404-1408 may be stored in a remote server (e.g., data store servers 304 of FIG. 3), and may be used as a basis for calculating the title health score 1402 of the title, as will be described.

The chapter health score average metric 1404 may include a chapter health score average value that represents an average of the health scores of all chapters included in the corresponding title. An example of how a chapter health score average score may be determined from a chapter health score average value for a title is shown in the illustrative table 1420 of FIG. 14B. As shown, the chapter health score average score may be set equal to the chapter health score average value. The chapter health score average score may be used as a basis for determining the title health score 1402 for the corresponding title. The weight of the chapter health score average metric 1404 for a given chapter may be equal to 0.8. The reliability value of the chapter health score average metric for a given chapter may be equal to 1.

The chapter health score harmonic average metric 1406 may include a chapter health score harmonic average value that represents a weighted harmonic average of chapter health scores for all of the chapters included in the title. An example of how a chapter health score harmonic average score may be determined from a chapter health score harmonic average value for a title is shown in the illustrative table 1425 of FIG. 14C. The chapter health score harmonic average score may be used as a basis for determining the title health score 1402 for the corresponding title. The weight of the chapter health score harmonic average metric 1406 for a given title may be 0 if there is only one chapter in the given title, and 0.8 otherwise. The reliability value of the chapter health score harmonic average metric 1406 for a given title may be equal to 1.

The chapters usage metric 1408 may include a chapters usage value that represents a percentage of the number of chapters used (e.g., chapters for which at least one responder has submitted a response to at least one assessment item part of at least one assessment item of at least one section thereof) in the corresponding title to the total number of chapters available in that title. An example of how a chapters usage score may be determined from a chapters usage value for a section is shown in the illustrative table 1430 of FIG. 14D. As shown, the chapters usage score may be set to 0% for chapters usage values between 0% and 90%, and may increase from 0% to 100% as chapters usage values increase from 90% to 100%. The chapters usage score may be used as a basis for determining the title health score 1402 for the corresponding title. The weight of the chapter usage metric 1408 for a given title may be 0 if all chapters were used and 0.3 otherwise. The reliability value of the chapter usage metric 1408 for a given title may be 1.

The title health score 1402 may be determined based on the score, weight, and reliability value of each of the chapter-level metrics 1404-1408.

Figure 15:
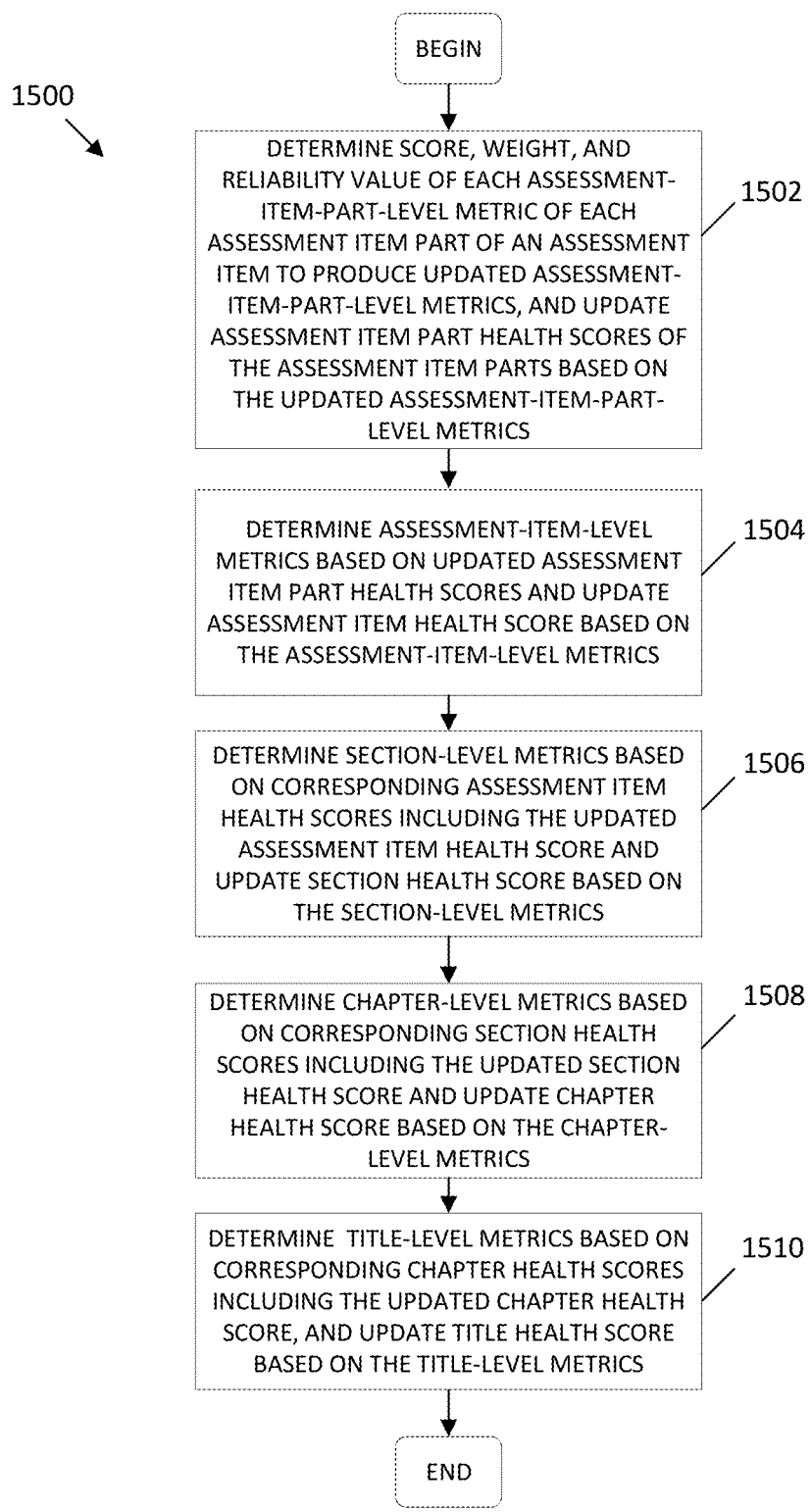
FIG. 15 illustrates a process flow diagram by which metrics and title, chapter, section, and assessment item health scores may be determined, in accordance with an embodiment.

FIG. 15 shows an illustrative process flow for a method 1500 by which title, chapter, section, assessment item, and assessment item part health scores (e.g., health scores 1102, 1202, 1302, and 1402 of FIGS. 11A, 12A, 13A, and 14A) may be determined for a corresponding title, chapter, section, assessment item, and assessment item part, respectively. For example, the steps of the method 600 may be performed by executing computer-readable instructions stored in one or more system memories (e.g., system memory 218, FIG. 2) and/or computer-readable storage media (e.g., computer-readable storage media 216, FIG. 2) using one or more computer processors (e.g., processing units 204, FIG. 2) of one or more computer systems (e.g., computer system 200, FIG. 2). In some embodiments, the method 1500 may be executed by one or more computer processors of one or more data store servers (e.g., data store servers 304), which may maintain and update data including KPIs and other metrics for one or more titles (e.g., title 902 of FIG. 9) and constituent chapters, sections, and assessment items of the one or more titles. The method 1500 may be performed, for example, periodically according to a predetermined schedule, or may be performed in response to the one or more computer systems determining that new response data is available for one or more of the assessment item parts of the assessment item.

At step 1502, the score, weight, and reliability value of each assessment-item-part-level metric of each assessment item part of an assessment item may be determined in order to produce updated assessment-item-part-level metrics (e.g., assessment-item-part-level metrics 1002-1016 of FIG. 10A) for each assessment item part of the assessment item (e.g., according to Eqs. 3-7). Updated assessment item part health scores may be determined for each assessment item part of the assessment item based on the updated assessment-item-part-level metrics (e.g., according to Eq. 8).

At step 1504, the score, weight, and reliability value of each assessment-item-level metric of the assessment item may be determined based on the updated assessment item part health scores, assessment item usage metrics, and assessment item part usage metrics in order to produce updated assessment-item-level metrics (e.g., assessment-item-level metrics 1104-1116 of FIG. 11A) the assessment item. An updated assessment item health score may be determined for the assessment item based on the updated assessment-item-level metrics (e.g., according to Eq. 8).

At step 1506, the score, weight, and reliability value of each section-level metric of a section that includes the assessment item may be determined based on corresponding assessment item health scores including the updated assessment item health score, section usage metrics, and assessment item usage metrics in order to produce updated section-level metrics (e.g., section-level metrics 1204-1210 of FIG. 12A) for the section. An updated section health score may be determined for the section based on the updated section-level metrics (e.g., according to Eq. 8).

At step 1508, the score, weight, and reliability value of each chapter-level metric of a chapter that includes the section may be determined based on corresponding section health scores including the updated section health score, assessment item health scores including the updated assessment item health score, section usage metrics, and chapter usage metrics in order to produce updated chapter-level metrics (e.g., chapter-level metrics 1304-1312 of FIG. 13A) for the chapter. An updated chapter health score may be determined for the chapter based on the updated chapter-level metrics (e.g., according to Eq. 8).

At step 1510, the score, weight, and reliability value of each title-level metric of a title that includes the chapter may be determined based on corresponding chapter health scores including the updated chapter health score and chapter usage metrics in order to produce updated chapter-level metrics (e.g., title-level metrics 1404-1412 of FIG. 14A) for the chapter. An updated chapter health score may be determined for the chapter based on the updated chapter-level metrics (e.g., according to Eq. 8).

The updated assessment-item-part-, assessment-item-, section-, chapter-, and title-level metrics and the updated assessment item part, assessment item, section, chapter, and title health scores determined via the execution of the method 1500 may be stored in a computer database of a server (e.g., server 304 of FIG. 3). One or more client devices (e.g., client devices 106 of FIG. 1) may subsequently retrieve the updated metrics and health scores from the database of the server via a connection to the server through a communication network (e.g., communication network 120 of FIG. 1). The retrieved metrics and health scores may be used generate corresponding user interfaces (e.g., user interfaces 1000, 1100, 1200, 1300, and/or 1400, of FIGS. 10A, 11A, 12A, 13A, and 14A) displayed on one or more electronic displays of the one or more client devices, so that a user of one of the client devices may quickly and efficiently identify any underperforming titles, chapters, sections, assessment items, and assessment item parts.

While many specific metrics, metric values, metric scores, weights, and reliability scores have been described above, it should be understood that these are intended to be illustrative and not limiting. If desired, other applicable metrics, metric values, metric scores, weights, and reliability scores may be used in the calculation of content health scores. Additionally, it should be understood that the hierarchical levels of title, chapter, section, assessment item, and assessment item part described herein are intended to be illustrative and not limiting. If desired, content health scores and metric scores, weights, and reliability values may be determined for other applicable hierarchical levels or organizational paradigms for digital assessment content (e.g., levels including title, unit, activity, and task).

Other embodiments and uses of the above inventions will be apparent to those having ordinary skill in the art upon consideration of the specification and practice of the invention disclosed herein. The specification and examples given should be considered exemplary only, and it is contemplated that the appended claims will cover any other such embodiments or modifications as fall within the true scope of the invention.

The Abstract accompanying this specification is provided to enable the United States Patent and Trademark Office and the public generally to determine quickly from a cursory inspection the nature and gist of the technical disclosure and in no way intended for defining, determining, or limiting the present invention or any of its embodiments.

The invention claimed is:

1. A system comprising:
   a computer processor;
   an electronic communication network, the computer processor being in electronic communication with a client computer device via the electronic communication network;
   a source database in electronic communication with the computer processor that stores assessment data corresponding to a plurality of assessment items; and
   a computer memory in electronic communication with the computer processor and configured to store computer-readable instructions which, when executed by the computer processor cause the computer processor to:
   retrieve the assessment data from a source database;
   determine first assessment item part health scores for each of a plurality of assessment item parts of an assessment item of the plurality of assessment items, determining an assessment item part health score for an assessment item part of the plurality of assessment item parts comprising:
   determining assessment-item-part-level metric values for a plurality of assessment-item-part-level metrics for the assessment item part based on responses submitted to the plurality of assessment item parts by a sample population of responders, wherein determining the assessment-item-part-level metric values for the plurality of assessment-item-part-level metrics for the assessment item part based on responses submitted to the plurality of assessment item parts by the sample population of responders comprises:
  determining a difficulty metric value, a discrimination metric value, and a hint change metric value for the assessment item part based on the assessment data and a modified two-parameter item response theory model;
  determining assessment-item-part-level metric scores for each of the plurality of assessment-item-part-level metrics based on the assessment-item-part-level metric values;
  assigning assessment-item-part-level weight values to each of the plurality of assessment-item-part-level metrics;
  determining assessment-item-part-level reliability values for each of the plurality of assessment-item-part-level metrics based on at least a size of the sample population of responders; and
  determining the assessment item part health score for the assessment item part based on the assessment-item-part-level metric scores, the assessment-item-part-level weight values, and the assessment-item-part-level reliability values;
generate a first user interface that includes the assessment-item-part-level metric scores; and
cause the first user interface to be displayed at a screen of the client computer device.

2. The system of claim 1, wherein the computer-readable instructions, when executed by the computer processor cause the computer processor to:
determine an assessment item health score for the assessment item by:
  determining assessment-item-level metric values for a plurality of assessment-item-level metrics for the assessment item based at least on the first assessment item part health scores;
  determining assessment-item-level metric scores for each of the plurality of assessment-item-level metrics based on the assessment-item-level metric values;
  assigning assessment-item-level weight values to each of the plurality of assessment-item-level metrics;
  determining assessment-item-level reliability values for each of the plurality of assessment-item-level metrics; and
  determining the assessment item health score for the digital assessment item based on the assessment-item-level metric scores, the assessment-item-level weight values, and the assessment-item-level reliability values;
generate a second user interface that includes the assessment item health score and the assessment-item-level metric scores; and
cause the second user interface to be displayed at the client computer device.

3. The system of claim 2, wherein the plurality of assessment-item-part-level metrics comprise at least a difficulty metric, a discrimination metric, and a hint change metric, wherein the difficulty metric corresponds to an estimate of assessment item part difficulty, wherein the discrimination metric corresponds to an estimate of an ability of a given assessment item part to discriminate between responders having different ability levels, and wherein the hint change metric corresponds to an estimate of how assessment item part difficulty is affected by hint usage.

4. The system of claim 2, wherein the assessment-item-level metrics include one or more of:
  an assessment item usage metric corresponding to a percentage of responders that used the assessment item to all responders that used assessment items in a section, the section comprising the assessment item;
  an assessment item completion metric corresponding to a percentage of responders that completed the assessment item to all responders that used the assessment item;
  a difference in assessment item part usage metric corresponding to a difference between a first number of responders that submitted at least one response to a most often used assessment item part of the assessment item and a second number of responders that submitted at least one response to a least often used assessment item part of the assessment item;
  an unused assessment item part metric corresponding to a percentage of unused assessment item parts of the assessment item;
  an assessment item part health score difference metric corresponding to an average difference between each of a plurality of assessment item part health scores corresponding to the assessment item, the plurality of assessment item part health scores including the first assessment item part health scores;
  an assessment item alignment metric corresponding to an estimate of how completing a formative assessment item of the assessment items affects responder performance on a corresponding summative assessment item of the assessment items; and
  an assessment item part health score average metric corresponding to an average of the plurality of assessment item part health scores.

5. The system of claim 1, wherein determining the difficulty metric value, the discrimination metric value, and the hint change metric value for the assessment item part comprises:
  iteratively applying a gradient descent optimization algorithm and a loss function to at least a portion of the assessment data according to the modified two-parameter item response theory model to determine the difficulty metric value, the discrimination metric value, and the hint change metric value.

6. The system of claim 5, wherein the loss function comprises a sum of a cross entropy component, an ability mean component, and an ability standard deviation component.

7. The system of claim 1, wherein at least a portion of the assessment-item-part-level metric values are calculated by first and second general purpose graphics processing unit instances operating in parallel.

8. A system comprising:
a computer processor;
a source database in electronic communication with the computer processor that stores assessment data corresponding to a plurality of assessment items; and
a computer memory in electronic communication with the computer processor and configured to store computer-readable instructions which, when executed by the computer processor cause the computer processor to:
  retrieve the assessment data from the source database;
  determine a content health score for content of a hierarchical content level by:
    determining metric values for a plurality of metrics for the content based on responses submitted to one or more of the plurality of digital assessment items by a sample population of responders, the plurality of metrics corresponding to the hierarchical content level of the content,
wherein determining the metric values for the plurality of metrics for the content based on responses submitted to one or more of the plurality of digital assessment items by the sample population of responders:
determining a difficulty metric value, a discrimination metric value, and a hint change metric value for the content based on the assessment data and a modified two-parameter item response theory model;
determining metric scores for the plurality of metrics based on the metric values;
assigning respective weight values to each of the plurality of metrics for the content;
determining respective reliability values for each of the plurality of metrics; and
determining the content health score for the content based on the metric scores, the weight values, and the reliability values;
generate a user interface that includes the content health score and the metric scores; and
cause the user interface to be displayed at a screen of a client computer device in electronic communication with the computer processor.

9. The system of claim 8, wherein determining respective reliability values for each of the plurality of metrics comprises:
determining respective reliability values for each of the plurality of metrics for the content based on at least a size of the sample population of responders.

10. The system of claim 9, wherein determining the content health score for the content based on the metric scores, the weight values, and the reliability values comprises:
calculating a first term by:
calculating a first plurality of products, wherein each of the first plurality of products corresponds to a respective metric of the plurality of metrics for the content, and wherein the first plurality of products comprises a first product of a metric score of the metric scores, a weight value of the weight values, and a reliability value of the reliability values; and
calculating a first sum of the first plurality of products;
calculating a second term by:
calculating a second plurality of products, wherein each of the second plurality of products corresponds to a respective metric of the plurality of metrics for the content, and wherein the second plurality of products comprises a second product of the weight value and the reliability value; and
calculating a second sum of the second plurality of products; and
dividing the first term by the second term.

11. A method comprising:
with a processor, retrieving assessment data from a source database, the assessment data corresponding to a plurality of digital assessment items;
determining first assessment item part health scores for each of a plurality of assessment item parts of an assessment item of the plurality of assessment items, wherein determining an assessment item part health score for an assessment item part of the plurality of assessment item parts comprises:
with the processor, determining assessment-item-part-level metric values for a plurality of assessment-item-part-level metrics for the assessment item part based on responses submitted to the plurality of assessment item parts by a sample population of responders,
wherein determining the assessment-item-part-level metric values for the plurality of assessment-item-part-level metrics for the assessment item part based on responses submitted to the plurality of assessment item parts by the sample population of responders comprises:
with the processor, determining a difficulty metric value, a discrimination metric value, and a hint change metric value for the assessment item part based on the assessment item data and a modified two-parameter item response theory model;
with the processor, determining assessment-item-part-level metric scores for each of the plurality of assessment-item-part-level metrics based on the assessment-item-part-level metric values;
with the processor, assigning assessment-item-part-level weight values to each of the plurality of assessment-item-part-level metrics;
with the processor, determining assessment-item-part-level reliability values for each of the plurality of assessment-item-part-level metrics based on at least a size of the sample population of responders; and
with the processor, determining the assessment item part health score for the assessment item part based on the assessment-item-part-level metric scores, the assessment-item-part-level weight values, and the assessment-item-part-level reliability values;
with the processor, generating a first user interface that includes the assessment-item-part-level metric scores; and
with the processor, causing the first user interface to be displayed at a client computer device.

12. The method of claim 11, further comprising:
with the processor, determining an assessment item health score for the assessment item by:
with the processor, determining assessment-item-level metric values for a plurality of assessment-item-level metrics for the digital assessment item based at least on the first assessment item part health scores;
with the processor, determining assessment-item-level metric scores for each of the plurality of assessment-item-level metrics based on the assessment-item-level metric values;
with the processor, assigning assessment-item-level weight values to each of the plurality of assessment-item-level metrics;
with the processor, determining assessment-item-level reliability values for each of the plurality of assessment-item-level metrics; and
with the processor, determining the assessment item health score for the assessment item based on the assessment-item-level metric scores, the assessment-item-level weight values, and the assessment-item-level reliability values;
with the processor, generating a second user interface that includes the assessment item health score and the assessment-item-level metric scores; and
with the processor, causing the second user interface to be displayed at the client computer device.

13. The method of claim 12, wherein the plurality of assessment-item-part-level metrics comprise at least a difficulty metric, a discrimination metric, and a hint change metric, wherein the difficulty metric corresponds to an estimate of assessment item part difficulty, wherein the discrimination metric corresponds to an estimate of an ability of a given assessment item part to discriminate between responders having different abilities, and wherein the hint change metric corresponds to an estimate of how assessment item part difficulty is affected by hint usage.

14. The method of claim 12, wherein the assessment-item-level metrics include one or more of:
- an assessment item usage metric corresponding to a percentage of responders that used the assessment item to all responders that used assessment items in a section, the section comprising the digital assessment item;
- an assessment item completion rate metric corresponding to a percentage of responders that completed the digital assessment item to all responders that used the assessment item;
- a difference in assessment item part usage metric corresponding to a difference between a first number of responders that submitted at least one response to a most often used assessment item part of the assessment item and a second number of responders that submitted at least one response to a least often used assessment item part of the assessment item;
- an unused assessment item part metric corresponding to a percentage of unused assessment item parts of the assessment item;
- an assessment item part health score difference metric corresponding to an average difference between each of a plurality of assessment item part health scores corresponding to the assessment item, the plurality of assessment item part health scores including the first assessment item part health scores;
- an assessment item alignment metric corresponding to an estimate of how completing a formative assessment item of the assessment items affects responder performance on a corresponding summative assessment item of the assessment items; and
- an assessment item health score average metric corresponding to an average of the plurality of assessment item part health scores.

15. The method of claim 11, wherein determining the difficulty metric value, the discrimination metric value, and the hint change metric value for the assessment item part comprises:
- with the processor, iteratively applying a gradient descent optimization algorithm and a loss function to at least a portion of the assessment item data according to the modified two-parameter item response theory model to determine the difficulty metric value, the discrimination metric value, and the hint change metric value.

16. The method of claim 15, wherein the loss function comprises a sum of a cross entropy component, an ability mean component, and an ability standard deviation component.

17. The method of claim 11, wherein at least a portion of the assessment-item-part-level metric values are calculated by first and second general purpose graphics processing unit instances operating in parallel.

* * * * *